(12) United States Patent
Ruan et al.

(10) Patent No.: US 7,011,790 B2
(45) Date of Patent: *Mar. 14, 2006

(54) NON-THERMAL DISINFECTION OF BIOLOGICAL FLUIDS USING NON-THERMAL PLASMA

(75) Inventors: R. Roger Ruan, Arden Hills, MN (US); Hongbin Ma, St. Paul, MN (US); Paul L. Chen, Roseville, MN (US); Shaobo Deng, St. Paul, MN (US); Xiangyang Lin, Fuzhou (CN); Duane P.M. Oyen, Maple Grove, MN (US); Robert J. Bowman, Edina, MN (US)

(73) Assignee: Regents of The University of Minnesota, Mpls., MN (US)

( * ) Notice: Subject to any disclaimer, the term of this patent is extended or adjusted under 35 U.S.C. 154(b) by 23 days.

This patent is subject to a terminal disclaimer.

(21) Appl. No.: 10/426,605

(22) Filed: Apr. 30, 2003

(65) Prior Publication Data

US 2004/0022669 A1    Feb. 5, 2004

Related U.S. Application Data

(63) Continuation-in-part of application No. 10/364,599, filed on Feb. 11, 2003, which is a continuation-in-part of application No. 09/850,284, filed on May 7, 2001, now Pat. No. 6,562,386.

(60) Provisional application No. 60/377,130, filed on Apr. 30, 2002.

(51) Int. Cl.
*A61L 2/00*     (2006.01)

(52) U.S. Cl. ..................... 422/22; 422/99; 422/186.04; 422/186.05; 204/164

(58) Field of Classification Search ................. 422/22, 422/186.04, 186.05, 99; 204/164
See application file for complete search history.

(56) References Cited

U.S. PATENT DOCUMENTS

| 2,345,798 A | 4/1944 | Daily |
| 3,865,733 A | 2/1975 | Taylor ........................ 250/532 |
| 3,970,905 A | 7/1976 | Itoh et al. ................ 317/262 E |

(Continued)

FOREIGN PATENT DOCUMENTS

DE          43 32 866 A1      3/1995

(Continued)

OTHER PUBLICATIONS

Kimberly Kelly Wintenberg et al., Air Filter Sterilization Using a One Atmosphere Uniform Glow Discharge Plasma (the Volfilter), IEEE Transactions on Plasma Science, Feb. 2000, vol. 28, No. 1.

(Continued)

*Primary Examiner*—N. Bhat
(74) *Attorney, Agent, or Firm*—Westman, Champlin & Kelly

(57) ABSTRACT

A method and apparatus are provided for at least partially disinfecting biological fluid of a mammal, which comprises pathogens in addition to normal cellular fractions. The method includes placing the biological fluid in a reaction volume and contacting a non-thermal plasma with the biological fluid to thereby kill at least a portion of the pathogens within the biological fluid.

29 Claims, 27 Drawing Sheets

U.S. PATENT DOCUMENTS

| | | | |
|---|---|---|---|
| 4,085,170 A | 4/1978 | Simpson et al. ............... | 261/1 |
| 4,244,712 A | 1/1981 | Tongret ...................... | 55/124 |
| 4,391,773 A | 7/1983 | Flanagan ..................... | 422/22 |
| 4,863,701 A | 9/1989 | McMurray ............. | 422/186.08 |
| 5,304,486 A | 4/1994 | Chang ........................ | 435/287 |
| 5,326,530 A | 7/1994 | Bridges ...................... | 422/22 |
| 5,370,846 A | 12/1994 | Yokomi et al. ........ | 422/186.07 |
| 5,411,713 A | 5/1995 | Iwanaga ............... | 422/186.15 |
| 5,427,747 A | 6/1995 | Kong et al. ................. | 422/186 |
| 5,458,748 A | 10/1995 | Breault et al. .............. | 204/177 |
| 5,516,493 A | 5/1996 | Bell et al. ............. | 422/186.07 |
| 5,549,874 A | 8/1996 | Kamiya et al. ........ | 422/186.04 |
| 5,603,893 A | 2/1997 | Gundersen et al. ........... | 422/22 |
| 5,637,198 A | 6/1997 | Breault ....................... | 204/165 |
| 5,670,122 A | 9/1997 | Zamansky et al. .......... | 423/210 |
| 5,681,533 A | 10/1997 | Hiromi ....................... | 422/121 |
| 5,695,619 A | 12/1997 | Williamson et al. ........ | 204/165 |
| 5,711,147 A | 1/1998 | Vogtlin et al. ................ | 60/274 |
| 5,746,984 A | 5/1998 | Hoard ........................ | 422/169 |
| 5,750,823 A | 5/1998 | Wofford et al. ............. | 588/210 |
| 5,759,497 A | 6/1998 | Kuzumoto et al. .... | 422/186.07 |
| 5,822,981 A | 10/1998 | Williamson et al. .......... | 60/275 |
| 5,836,154 A | 11/1998 | Williamson et al. .......... | 60/275 |
| 5,843,288 A | 12/1998 | Yamamoto .................. | 204/164 |
| 5,843,383 A | 12/1998 | Williamson et al. ... | 422/186.04 |
| 5,855,855 A | 1/1999 | Williamson et al. ... | 422/186.04 |
| 5,871,703 A | 2/1999 | Alix et al. .................. | 423/210 |
| 5,876,663 A * | 3/1999 | Laroussi ..................... | 422/23 |
| 5,891,409 A | 4/1999 | Hsiao et al. ............. | 423/239.1 |
| 5,893,267 A | 4/1999 | Vogtlin et al. ................ | 60/274 |
| 5,895,558 A | 4/1999 | Spence ....................... | 204/164 |
| 5,895,632 A | 4/1999 | Nomura et al. ........ | 422/186.04 |
| 5,904,905 A | 5/1999 | Dolezal et al. ........ | 422/186.04 |
| 6,030,506 A | 2/2000 | Bittenson et al. ........... | 204/164 |
| 6,096,564 A | 8/2000 | Denes et al. ................... | 438/1 |
| 6,146,599 A | 11/2000 | Ruan et al. ............ | 422/186.04 |
| 6,171,450 B1 | 1/2001 | Behnisch et al. ........... | 204/164 |
| 6,176,078 B1 | 1/2001 | Balko et al. .................. | 60/274 |
| 6,228,330 B1 | 5/2001 | Herrmann et al. ..... | 422/186.05 |
| 6,451,252 B1 * | 9/2002 | Ruan et al. .................... | 422/22 |
| 6,455,014 B1 * | 9/2002 | Hammerstrom et al. ...................... | 422/186.04 |
| 6,558,638 B1 | 5/2003 | Zadiraka et al. ....... | 422/186.04 |
| 6,562,386 B1 * | 5/2003 | Ruan et al. .................. | 426/237 |
| 6,818,193 B1 * | 11/2004 | Christodoulatos et al. .. | 423/210 |
| 3,898,468 A1 | 8/2005 | Guerin ....................... | 250/535 |
| 2003/0132100 A1 * | 7/2003 | Crowe et al. ............... | 204/164 |
| 2003/0180421 A1 * | 9/2003 | Ruan et al. ................. | 426/237 |

FOREIGN PATENT DOCUMENTS

| | | |
|---|---|---|
| DE | 196 35 231 A1 | 3/1998 |
| EP | 0 287 480 | 4/1988 |
| EP | 19717169 A1 | 10/1998 |
| FR | 2 759 590 | 2/1997 |
| GB | 2316017 | 2/1998 |
| JP | 59-69404 | 4/1984 |
| JP | 2-211218 | 8/1990 |
| JP | 2-211219 | 8/1990 |
| JP | 4-122417 | 4/1992 |
| JP | 4-247218 | 9/1992 |
| JP | 5-15736 | 1/1993 |
| JP | 07 256056 | 10/1995 |
| JP | 10-118448 | 5/1998 |
| JP | 10-235138 | 8/1998 |
| JP | 10-235138 | 9/1998 |
| JP | 2000093967 | 4/2000 |
| RU | XP-002140238 | 11/1996 |
| WO | WO 95/09256 | 4/1995 |
| WO | 980342 | 1/1998 |
| WO | WO 99/46201 | 9/1999 |
| WO | WO 01/52910 * | 7/2001 |
| WO | WO 01/52910 A1 | 7/2001 |

OTHER PUBLICATIONS

Thomas C. Montie et al., An Overview of Research Using the One Atmosphere Uniform Glow Discharge Plasma (OAUGDP) For Sterilization of Surfaces and Materials, IEEE Transactions on Plasma Science, Feb. 2000, vol. 28, No. 1.

J. Reece Roth et al., A Remote Exposure Reactor (RER) for Plasma Processing and Sterilization by Plasma Active Species at One Atmosphere, IEEE Transactions on Plasma Science, Feb. 2000, vol. 28., No. 1.

Joseph G. Birmingham et al., Bacterial Decontamination Using Ambient Pressure Nonthermal Discharge, IEEE Transactions on Plasma Science, Feb. 2000, vol. 28, No. 1.

K. Kelly-Wintenberg et al., Use of a One Atmosphere Uniform Glow Discharge Plasma to Kill a Broad Spectrum of Microorganisms, J. Vac. Sci. Technol., Jul./Aug. 1999.

Database WPI, Section Ch, Week 200123, KR 2000053 747 A( Human Mediteck Co Ltd), (report XP-002327531), Derwent Publications Ltd., London, G.B., 2001-223586, Sep. 5, 2000.

* cited by examiner

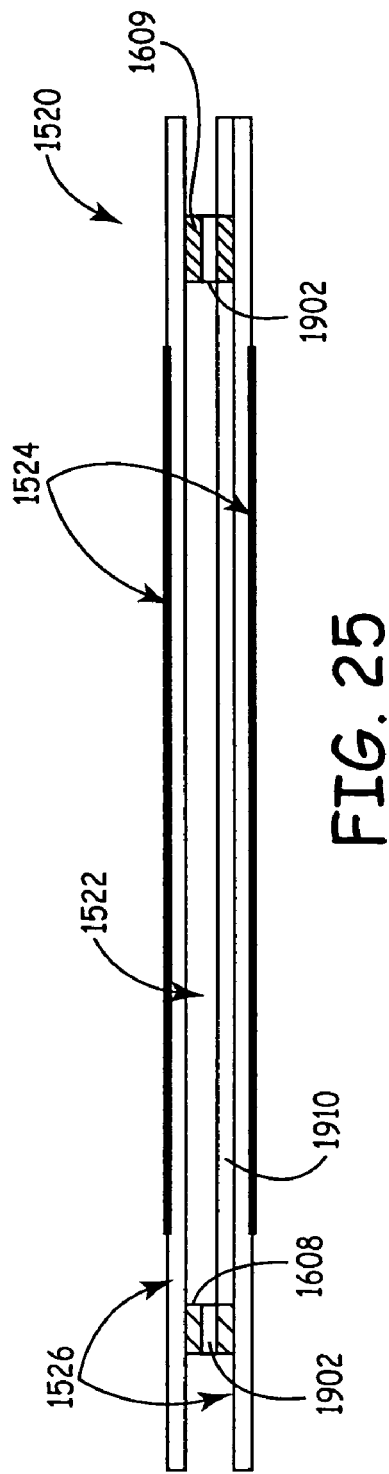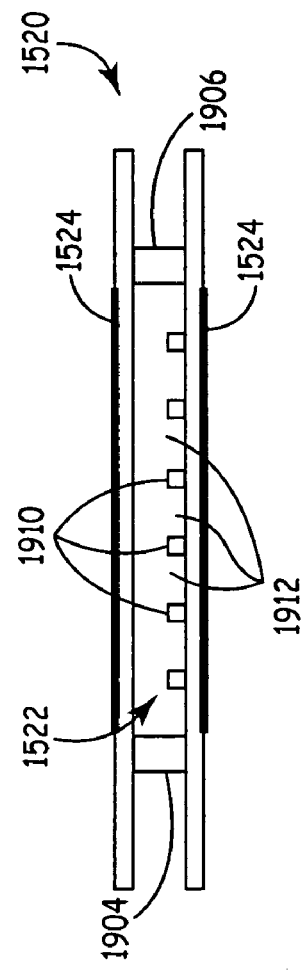

Plasma hemoglobin as a function of treatment time

White blood cell as a function of treatment time
(Ref. Range: 4.1 - 11.3 x 10³/uL)

Red blood cell as a function of treatment time
(Ref. Range: 5.52 - 8.48 x 10⁶/uL)

Total Plasma Protein as a function of treatment time
(Ref. Range: 6.8 - 9.2 g/dL)

Fibrinogen as a function of treatment time
(Ref. Range: 0.1 - 0.74 g/dL)

NON-THERMAL DISINFECTION OF BIOLOGICAL FLUIDS USING NON-THERMAL PLASMA

CROSS-REFERENCE TO RELATED APPLICATIONS

This application claims the benefit of U.S. Provisional Application No. 60/377,130, filed Apr. 30, 2002, and is a continuation-in-part of U.S. application Ser. No. 10/364,599, filed Feb. 11, 2003 now U.S. Pat. No. 6,911,225 and entitled "METHOD AND APPARATUS FOR NON-THERMAL PASTEURIZATION OF LIVING-MAMMAL INSTILLABLE LIQUIDS," which is a continuation-in-part of U.S. application Ser. No. 09/850,284, filed May 7, 2001 now U.S. Pat. No. 6,562,386 and entitled "METHOD AND APPARATUS FOR NON-THERMAL PASTEURIZATION."

FIELD OF THE INVENTION

The present invention relates to a method and apparatus for disinfection of biological fluids to cleanse the fluids of pathogenic microorganisms.

BACKGROUND OF THE INVENTION

The phenomenon of bacterial resistance through microevolutionary change has been well documented. Substantial concerns over the degrading effectiveness of classic broad spectrum antibiotics, such as penicillin and its analogues, as the microbes have adapted new protection mechanisms, has led to medical protocols that attempt to minimize their usage. The goal is to delay the time when larger segments of the population may find the effectiveness of critically needed antibiotics compromised for their needs. To delay this problem, such powerful anti-microbial agents as Vancomycin are prescribed only under the most stringent use protocols. In addition, there are few pharmacological compounds that have been found to be effective for treatment of viruses, and the few that exist are very strain-specific.

The pharmaceutical industry is desperately seeking new ways to battle infection. The myriad attempts to develop improved types of antibotics and anti-viral agents include mechanisms ranging from various innovative chemical inactivation mechanisms, gene-based techniques of drug production, and tailored anti-infective medications for individual patients. What all of these approaches have in common is that they are chemical: drugs that are ingested and then act biochemically on the host. The disadvantage is that, while the pathogens may be destroyed, the patient may also be compromised or worse, due to drug toxicity.

A further problem is that, in general for a severe systemic infection, there still exist antibiotic drugs that can effectively destroy bacterial pathogens. However, what often kills the patient are the toxic poisons that are released by the bacteria as they are lysed (destroyed) due to either immune system action or antibiotic effects. There are two categories of such substances: endotoxins, lipopolysaccharides that are associated with the cellular walls of gram-negative bacteria, and exotoxins, soluble proteins which are diffusible and may act at different sites from the bacterial invasion as some of the most potent poisons known, comparable to strychnine and snake venom. It may help the patient very little to destroy a bacterium that leaves a parting gift of poison for the host as it dies. A treatment is needed that has the potential to both destroy bacteria in biological fluids such as blood, and also allow toxins to be filtered out of the blood before they can injure the patient. This phenomenon is applicable to both humans and animals.

Various methods of non-chemical purification of biological fluids, medicines, vaccines, etc., have been proposed to destroy or inactivate pathogens, including bacteria, viruses, and fungi, in the liquids. These methods typically generate heat during the purification process and may introduce impurities depending on the process. This heat can easily damage the active ingredients or critical live tissues that perform the essential functions of the fluids. In the case of biological fluids, if these tissues are thermally processed, they may become non-functional, as in the case of some clotting compounds, or vital living cells such as erythrocytes (red blood cells, RBC) or leukocytes (white blood cells, WBC) may be altered or damaged in ways that both mar instant function or compromise cellular stability, hardiness, or reproduction. When treating delicate biological fluids such as blood, these processes have had marginal success because blood functions properly in a very narrow temperature range around the normal 37 degrees C. (nominally 98.6 degrees F.).

Blood that is drawn from donors and banked for transfusion currently must go through multiple exhaustive steps to ensure safety for use, and there are large volumes of scarce blood and plasma that must be destroyed when they are found to be contaminated. A pasteurization technology that is able to cycle fluids such as blood through an apparatus outside the body to destroy the bacterial infection, and then filter out the toxins released in the process, and permit blood or plasma to be safely used rather than wasted will provide significant benefit to the health care system. Such a safe and efficacious technology should also permit cost-saving protocol changes in the collection and handling of biological fluids such as blood.

A number of minimal thermal processes have been developed for some of these applications, including ultra-filtration, ozonation, pulsed ultraviolet light, irradiation, high hydrostatic pressure (HHP) and pulsed electric field (PEF) discharge.

PEF discharge has been shown to be very effective for killing bacteria within medically useful liquids that are not subject to degradation, such as vaccines, medications, and other sterile substances. PEF discharge is considered to be one of the premier new technologies with a great potential of replacing thermal, chemical and other pasteurization and sterilization technologies. However, there are a number of drawbacks of the PEF discharge technology. For example, ohmic heating still occurs during the PEF discharge, which causes the temperature of the liquid being treated to rise. Hence, a cooling system must be used in order to maintain the liquid at a low temperature. A significant amount of energy is wasted with unwanted heating and cooling of the liquid. Also, the requirement of a cooling system adversely increases the time required to treat the liquid. In addition, the PEF electrodes are immersed directly in the liquid. Since the electrodes contact the liquid, they are regarded as a major contamination source to the liquid due to oxidation of the electrodes during discharge. The electrodes must therefore be replaced regularly, which increases maintenance time and costs.

With respect to ozonation, numerous research reports have demonstrated the antiviral effect of ozone exposure. For example, K. H. Wells, J. Latino, J. Gavalchin and B. J. Poiesz, *Blood*, 78, 1882–90 (1991), reported more than 11 logs inactivation of HIV-1 virus in human blood that was exposed to ozone at a concentration of 1,200 ppm for two hours. J. M. Vaughn, Y. S. Chen, K. Lindburg and D. Morales, *Appl. Environ. Microbiol.*, 53, 2218–21 (1987), reported the use of ozone to inactivate simian rotavirus SA-11 and human rotavirus type 2 (Wa) at 4° C. by using single-particle virus stocks, and found that although the human strain was clearly more sensitive; both virus types were rapidly inactivated by ozone concentrations of 0.25 mg/liter or greater at all pH levels tested.

Use of ozone to kill viruses in blood and blood products has received increasing attention in the medical field, due to its high effectiveness, cost efficiency, and simplicity, with minimal collateral damage to blood cellular metabolism. Ozone is a strong oxidative, and can react with blood to form compounds which are identical to those produced by a human's own immune system to destroy viruses and bacteria. Some of these compounds include oxygen atoms, hydrogen peroxide, and lipid peroxide. Research in the Wells et al. article has indicated that the antiviral effects of ozone include viral particle disruption, reverse transcriptase inactivation, and/or a perturbation of the ability of the virus to bind to its receptor on target cells. Based on a study on the mechanism of enteroviral inactivation by ozone with poliovirus 1 as the model virus, D. Roy, P. K. Wong, R. S. Engelbrecht and E. S. Chian, *Appl. Environ. Microbiol.*, 41, 718–23 (1981) concluded that the damage to the viral nucleic acid is the major cause of poliovirus 1 inactivation by ozone.

In addition, use of ozone is entering commercial practice for purification of bottled water, but requires strict limitation of its concentration because of concerns over potential formation of the suspected carcinogen bromate when excess ozone concentration is permitted to interact with minerals in the water. This becomes an even greater concern when treating biological fluids, such as blood products since ozone can dissolve in the water of the blood plasma and therefore remain for an extended period of time. With biological fluids, the ozone must therefore be "inactivated" through the passage of time or by some other method. The lingering ozone may be an advantage for purifying bottled water, but in biological fluids, control of all biochemical process is critical.

Thus, while ozone and other minimally thermal methods are being researched for treatment of biological fluids, improved methods are desired for treating biological fluids such as blood without degrading their natural characteristics or generating toxic byproducts.

SUMMARY OF THE INVENTION

One embodiment of the present invention is directed to a method for at least partially disinfecting biological fluid of a mammal, which comprises pathogens in addition to normal cellular fractions. The method includes placing the biological fluid in a reaction volume and contacting a non-thermal plasma with the biological fluid to kill at least a portion of the pathogens within the biological fluid.

Another embodiment of the present invention is directed to a circulating blood disinfection apparatus for at least partially disinfecting blood of a mammal. The apparatus includes first and second shunts for coupling to a circulatory system of the mammal, an inlet path coupled to a blood outlet of the first shunt for carrying the blood to be disinfected, and an outlet path coupled to a blood inlet of the second shunt for returning the blood to the mammal. A non-thermal plasma reactor is coupled between the inlet and outlet paths. The reactor includes first and second electrodes, at least one dielectric barrier between the first and second electrodes, and a reaction volume between the first and second electrodes and coupled to the inlet path and the outlet path.

Another embodiment of the present invention is directed to a probe for insertion into a mammal. The probe has a shaft with a proximal end, a distal end, and an inlet and an outlet. A non-thermal plasma reactor is carried along the shaft and includes first and second electrodes, at least one dielectric barrier between the first and second electrodes, and a reaction volume between the first and second electrodes. The reaction volume is coupled to the inlet and the outlet.

Another embodiment of the present invention is directed to a biological fluid treatment apparatus. The apparatus includes a biological fluid input for receiving biological fluid of a mammal, a gas injector, a non-thermal plasma reactor, and a gas-liquid separator. The gas injector introduces gas bubbles into the biological fluid received from the biological fluid input to produce a mixture of the biological fluid and the gas bubbles. The non-thermal plasma reactor receives the mixture of the biological fluid and the gas bubbles within a reaction volume and generates a non-thermal plasma within the reaction volume to thereby kill at least a portion of pathogens within the biological fluid. The gas-liquid separator is coupled to an output of the reactor for separating the gas bubbles from the biological fluid.

Another embodiment of the present invention is directed to fluid, which includes a mammalian biological fluid and a non-thermal plasma.

BRIEF DESCRIPTION OF THE DRAWINGS

FIG. 24 is a cross-sectional view of the NTP cell, taken along lines 24—24 of FIG. 23.

FIG. 25 is a cross-sectional view of the NTP cell taken along lines 25—25 of FIG. 23.

DETAILED DESCRIPTION OF ILLUSTRATIVE EMBODIMENTS

Figure 1:
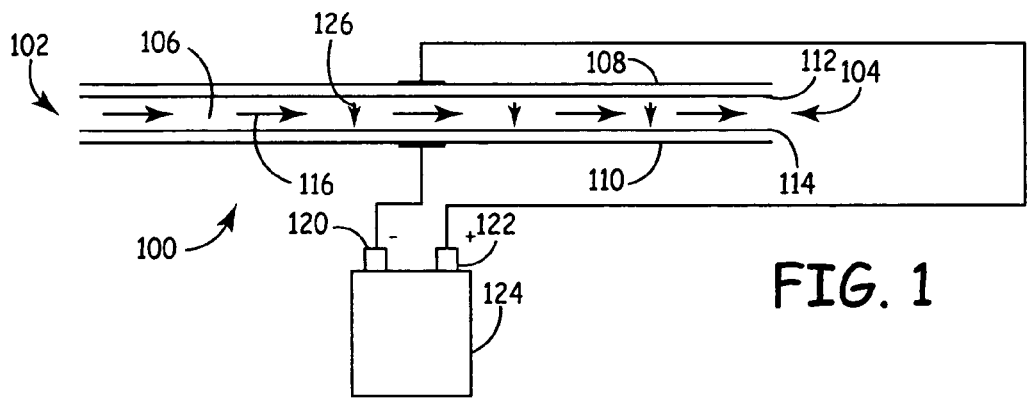
FIG. 1 is a diagrammatic view of a "silent type", volume discharge non-thermal plasma reactor, which can be used for disinfecting biological fluids to destroy live pathogens living in the fluids.

FIG. 1 is a diagrammatic view of a "silent type", volume discharge non-thermal plasma reactor 100, which can be used for pasteurizing and/or at least partially sterilizing or disinfecting living-mammal-instillable liquids, such as biological fluids, to kill live pathogens living in the liquids. Non-thermal plasma reactor 100 includes a liquid inlet 102, a liquid outlet. 104, a reaction volume 106 between liquid inlet 102 and liquid outlet 104, electrodes 108 and 110, and dielectric barriers 112 and 114. Flow path 116 indicates the liquid flow path from inlet 102 to outlet 104, through reaction volume 106. Each of the electrodes 108 and 110 is physically and electrically isolated from the liquid in flow path 112 by a respective one of the dielectric barriers 112 and 114.

Dielectric barriers 112 and 114 are separated from one another by a gap, which defines the effective width of reaction volume 106. Dielectric barriers 112 and 114 can include Teflon, glass, ceramic or epoxy resin, for example. Other insulating materials can also be used. In one embodiment, each electrode 108 and 110 is embedded within an epoxy resin. The discharge gap between electrodes 108 and 110 can be sized to suit a particular application. For example, electrodes 108 and 110 can be separated by a distance of up to 30 centimeters. A larger gap can be used if voltage and insulation conditions permit. In one particular embodiment, electrodes 108 and 110 are separated by 10 millimeters, with an effective gap between dielectric layers 112 and 114 of about 7 millimeters.

Electrodes 108 and 100 can have a variety of configurations. For example in the embodiment shown in FIG. 1, electrodes 108 and 110 are each formed of a thin, planar sheet of conductive metal, such as a copper foil. Other conductive structures can also be used such as a conductive mesh, wire or strip. The combination of electrodes 108 and 110 can have a variety of different types, such as plate-toplate, mesh-to-mesh, plate-to-wire, wire-to-wire, plate-to-mesh and wire-to-mesh, for example. The shapes of electrodes 108 and 110 can also be varied. For example, electrodes 108 and 110 can be arranged coaxially with one another, wherein the outer electrode is tubular and the inner electrode is either tubular or a wire. Other arrangements can also be used. However, in each arrangement, both electrodes 108 and 110 are physically and electrically isolated from the liquid in the reaction volume by a dielectric barrier in order to prevent an electrical conduction path through the liquid and contamination of the liquid due to contact with the electrodes.

High voltage power supply 124 supplies power to electrodes 108 and 110. Electrode 108 is electrically coupled to a first terminal 120 of power supply 124, and electrode 110 is electrically coupled to a second terminal 122 of power supply 124. One of the electrodes 108 and 110 serves a ground electrode, such as electrode 110, and the other, such as electrode 108, serves as a high voltage electrode. Power supply 124 can include a continuous direct-current (DC) or an alternating-current (AC) power supply that is capable of producing a voltage across electrodes 108 and 110 so as to form an electric discharge path, shown by arrows 126, across reaction volume 106. In one embodiment, the voltage potential generated between electrodes 108 and 110 is in the range of 1 kV–35 kV, for example. Other voltage ranges can also be used, such as voltage ranges between 1 kV and 500 kV. Power supply 124 can be operated at either low or high frequencies and can produce pulses with a single polarity or can produce bipolar pulses.

With electrodes 108 and 110 having opposite polarity, electrodes 108 and 110 generate a strong electrical field across reaction volume 106. The strong electrical field is applied to gas in the liquid, which generates non-thermal plasma species, including electrically neutral gas molecules, charged particles in the form of positive ions, negative ions, free radicals and electrons, and quanta of electromagnetic radiation (photons). Examples of the generation of these highly reactive species include, but are not limited to:

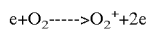
$e + O_2 \longrightarrow O_2^+ + 2e$

$O^+ + O + 2e$

$O^* + O + e$ $O^- + O$

$e + N_2 \longrightarrow N_2^+ + 2e$

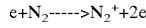
$N^+ + N + 2e$

$N_2^* + e$

$N^* + N + e$

$O^* + H_2O \longrightarrow 2OH$

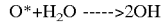
$O + O_2 + O_2 \longrightarrow O_3 + O_2$

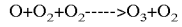
$e + H_2O \longrightarrow H + OH$

These non-thermal plasma species are highly reactive and are effective in destroying live pathogens, such as bacteria, viruses and fungi, living in the liquid being treated. The non-thermal plasma species are extremely strong oxidants that break down chemicals and kill microorganisms instantly. A non-thermal plasma is one in which the mean electron energy is much higher than that of the bulk-gas (or liquid) molecules. Energy is added to the electrons instead of the ions and bulk gas (or liquid) molecules. The electrons can therefore attain high energies, while the background molecules and ions remain at ambient temperature. Because of the non-thermal nature of reactor 100, reactor 100 preserves the quality and other heat-sensitive attributes of the liquids being disinfected.

Examples of liquids that can be treated include any liquid that is produced by or secreted by a living mammal, such as blood, tissue fluid, cerebrospinal fluid, or lymph; or a liquid that is biocompatible with the physiology of, and therefore beneficially instillable in a living mammal, such as a human, dog, horse, cat, etc. The term "instillable" includes all liquids that are non-toxic to a living mammal when introduced into the mammal by methods such as oral ingestion, inhaling, transdermal absorption, rectal (as with enema or other such solutions), direct insertion into arterial vessels, venal vessels (IV), lymphatic vessels, the spinal canal, and body cavities such as the abdomen, the lungs or the liver, intramuscular injection, and subcutaneous injection.

One example of such a liquid is a liquid that is capable of being consumed and assimilated by a living mammal as nourishment. Other treatable liquids may include fermentation broth, medications and vaccines of all types, total parenteral nutrition (TPN) liquids, including sugars and lipids, etc., intravenous (IV) fluids such as Lactated Ringers or D5, etc., renal dialyzing fluids (which are instilled and drawn back off), and biological fluids that must be returned to the body without damage to viable components such as platelets and leukocytes. These biological fluids can include heat-sensitive fluids such as human and animal bloods, blood products, such as plasma or lymph, extracellular tissue fluid, and cerebrospinal fluid (CSF).

Of these biologic fluids, the most important is blood, which brings the vital oxygen and nourishment to the organs of the body. When a mammal is infected with either a bacterial or viral pathogen, the blood is the carrier. Bacteria feed on the blood elements and reproduce uncontrollably; virus enters the blood cells and reproduces, but free virus is also carried throughout the body to contaminate other types of cells. The mammal's immune system combats and destroys the pathogens, but serious infections can overwhelm the body's immune system and compromise the innate ability to recover.

Blood is made up of plasma, the saline-and-water-based liquid that dissolves electrolytes such as sodium, calcium, and potassium, lipids, and vitamins, and carries the red blood cells (RBC, or erythrocytes), white blood cells (WBC, or leukocytes), and platelets (clot-supporting cells). Other minor fractions include hormones, antibodies, and albumin. But, when an infection occurs, the critical issue is cleansing the plasma, preventing it from carrying the infectious agents throughout the body, and choking off the major blood cell functions. Generally, lipids, electrolytes, vitamins, and other nutrients can be added intravenously as long as there is a minimal level of viable blood plasma and healthy cells to carry out basic functions. When blood volume is low, frequently fresh frozen plasma is added to increase blood volume.

Electrically-generated non-thermal plasma species can be used to inactivate pathogenic and spoilage microorganisms under "ambient" conditions, such as ambient temperature and atmospheric pressure or in non-ambient conditions. In one embodiment, "ambient" refers to the body's environment of approximately 37 degrees C. Non-thermal plasma is not the same substance as blood plasma. The term "non-thermal plasma" used in the specification and claims refers to a state of matter, such as a gas, atmosphere or liquid to which a specific amount of energy has been added to separate the component molecules into a collection of ions, electrons, free radicals, charge-neutral molecules, and other species in varying degrees of excitation. The term "blood plasma" refers to a saline and water carrier of the various blood fractions.

The non-thermal plasma used in this embodiment is a true non-thermal process, which disinfects or sterilizes biological fluids at the temperature of the host organism, but does not appear to pose a threat to the desirable properties of the fluids. For example, a five-log reduction in bacteria such as *Escherichia coli* and *Salmonellae* inoculated in biological fluids such as blood can be achieved with non-thermal plasma. As described in more detail below, hematology and morphology studies have shown that non-thermal plasma treatment does not cause significant changes in blood properties. The values for blood cell count, plasma hemoglobin, coagulation profile, and morphology of the treated blood samples were within the normal ranges following treatment.

In one embodiment of the present invention, it has been found that the reduction in pathogens living in the liquid being treated can be greatly enhanced if fine gas bubbles are introduced into the liquid being treated by the non-thermal plasma. The interaction of gas bubbles with the non-thermal plasma has been found to enhance the disinfection effectiveness by significantly enhancing the exposure of the host fluid to the highly reactive NTP species. The resulting liquid-gas mixture can include a gas dispersed in a liquid or a liquid dispersed in a gas. The gas can be mixed with the liquid in a variety of ways, such as by diffusion or injection. Various gas injection devices can be used, such as a Venturi tube gas injector made by Mazzei Injector Corporation. Alternatively, the liquid can be sprayed through the reaction chamber to form droplets of liquid separated by gas. In one embodiment, the liquid-gas mixture has a thickness along flow path 116 of 0.1 millimeters to 30 millimeters, for example. Other thicknesses can also be used. Reactor 100 can be constructed in various arrangements to expose the liquid-gas mixture to the plasma discharge for any treatment time, such as between 0.1 second to 10 minutes, for example. Other treatment times can also be used.

Introducing fine gas bubbles into the liquid greatly enhances the generation of plasma in reactor 100 for killing pathogens living in the liquid being treated. As the gas-liquid mixture is passed through NTP reactor 100, the gas bubbles in the liquid become excited by the applied electric field, generating non-thermal plasma. The non-thermal plasma species then interact with and kill pathogens living in the liquid. Parameters associated with gas injection include composition of the gas, amount and distribution of the gas in the liquid, the size of the gas bubbles, velocity of the liquid relative to the physical motion of the gas, and the gas injector orifice size. Experiments have shown in liquid containing gas bubbles, especially with a gas containing 90% oxygen, bacteria kill is increased substantially as compared to the bacteria kill in liquid containing no gas bubbles.

Various factors that may affect the killing power of the reactive NTP species within reaction volume 106 include the ratio of gas to liquid (from very low to very high), size of gas bubbles, degree of mixing of gas and liquid, and compositions of the gas and liquid. Preferably, the system is adapted to obtain at least a one log, and more preferably at least a 5 log to 10 log reduction in pathogens living in the liquid. This is a highly controllable and scalable process. In general, the liquid flow rates as described in this embodiment are sufficient to permit the liquid to pass through consecutive NTP chambers, with a pathogen reduction of approximately one log per chamber, for example. Thus, liquid can cycle three, or five, or ten times, and the pathogen-inactivation effect is essentially proportional. A high gas-to-liquid ratio can be obtained by injecting the liquid into a gas phase. For example, it was observed that the killing power of the NTP species was greater with smaller gas bubbles than with larger gas bubbles. Also, it has been found that the more evenly the gas bubbles are distributed in the liquid, the more effective the non-thermal plasma generation and pathogen reduction. In one embodiment, the ratio of gas volume to liquid volume (Gas Volume/Liquid Volume) is preferably 0.1 to 20, more preferably 0.3 to 5, and most preferably 0.5 to 1. However, other ratios outside these ranges can also be used. A variety of gas compositions can be used, such as air, oxygen, ozone and nitrogen, or a mixture of these or other gases. One type of gas may be more effective than another in a particular application, depending on the type of liquid and the types of pathogens being killed. For example, the gas bubbles can consist of 100% by volume oxygen (e.g., $O_2$) or 100% by volume nitrogen.

Figure 2:
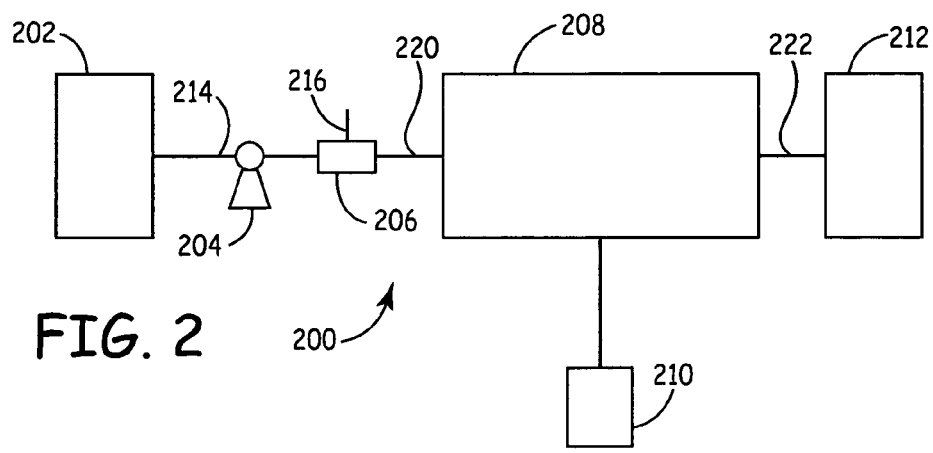
FIG. 2 is a diagram, which schematically illustrates a non-thermal plasma liquid disinfection system that introduces gas bubbles into the liquid being disinfected according to one embodiment of the present invention.

FIG. 2 is a diagram, which schematically illustrates a non-thermal plasma liquid pasteurization system 200 that introduces gas bubbles into the liquid according to one embodiment of the present invention. System 200 includes liquid source tank 202, pump 204, gas mixing device 206, non-thermal plasma reactor 208, high voltage power supply 210 and liquid receiving tank 212. Source tank 202, pump 204, gas mixing device 206, non-thermal plasma reactor 208 and receiving tank 212 are coupled in series with one another within a treatment flow path 214, which can be formed of a series of tubes or other liquid channels for passing the liquid to be treated from one element in path 214 to the next.

Tank 202 contains the liquid to be treated. Pump 204 pumps liquid from tank 202 to tank 212, through treatment flow path 214. Additional pumps can be placed at various locations along treatment flow path 214 in alternative embodiments. Also, pump 204 can be eliminated in embodiments in which another mechanism, such as gravity, is used for moving the liquid along treatment flow path 214. The output of pump 204 is coupled to the input of gas mixing device 206. The flow rate of the pump is set based on factors such as the desired treatment time, the applied voltage, the dimensions/structures of reactor 208, and the size of gas mixing device 206. Gas mixing device 206 can include any device that is capable of introducing gas bubbles into the liquid flowing through treatment flow path 214. Various mixing devices can be used, such as a gas diffuser or a gas injector. In one embodiment, gas mixing device 206 includes a Venturi tube injector. Other types of gas mixers can also be used. Gas mixing device 206 has a gas inlet 216 for receiving the gas to be mixed into the liquid.

The gas-liquid mixture is then provided to liquid inlet 220 of non-thermal plasma reactor 208. Reactor 208 can include reactor 100 shown in FIG. 1, for example. High voltage power supply 210 is electrically coupled to the electrodes within reactor 208. As the gas-liquid mixture passes through reactor 208, from liquid inlet 220 to liquid outlet 222, the non-thermal plasma generated in reactor 208 disinfects the liquid by destroying at least a portion of the live pathogens such as bacteria or viruses living in the liquid. The treated liquid then exits through liquid outlet 222 and is collected in receiving tank 212.

In one embodiment, the liquid being treated within reactor 208 is kept under a pressure that is greater than an ambient pressure surrounding the reactor so as to maintain the gas bubbles substantially uniformly distributed in the liquid and of a small size. The pressure can be increased by providing liquid outlet 222 with a cross-sectional area that is less than the cross-sectional area of liquid inlet 222. Also, the internal reactor flow path can be designed to provide a back pressure in the liquid and to provide turbulent flow.

Figure 3:
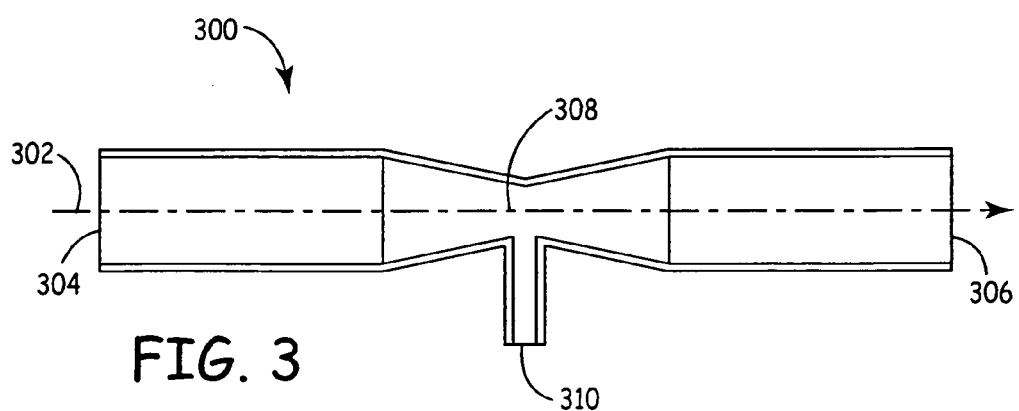
FIG. 3 is a diagram illustrating a Venturi tube injector, which can be used for introducing gas bubbles within the system shown in FIG. 2.

FIG. 3 is a diagram illustrating a Venturi tube injector 300, which can be used for the gas mixing device 204 shown in FIG. 2. Injector 300 has a main flow path 302 between an inlet 304 and an outlet 306 and has a flow constriction 308. A gas inlet 310 is coupled to the main flow path 302 at the flow constriction 308. As liquid flows along main flow path 302 a pressure difference between inlet 304 and outlet 306 creates a vacuum inside the injector body, which draws gas into the injector through gas inlet 310 and results in a mixture of gas and liquid at outlet 306. A Venturi tube injector is a high efficiency, differential pressure injector. It has been found that this type of injector mixes gases with liquids very well. As a result, bubbles in the gas-liquid mixture produced at the output of injector 300 are extremely fine and uniformly distributed.

Figure 4:
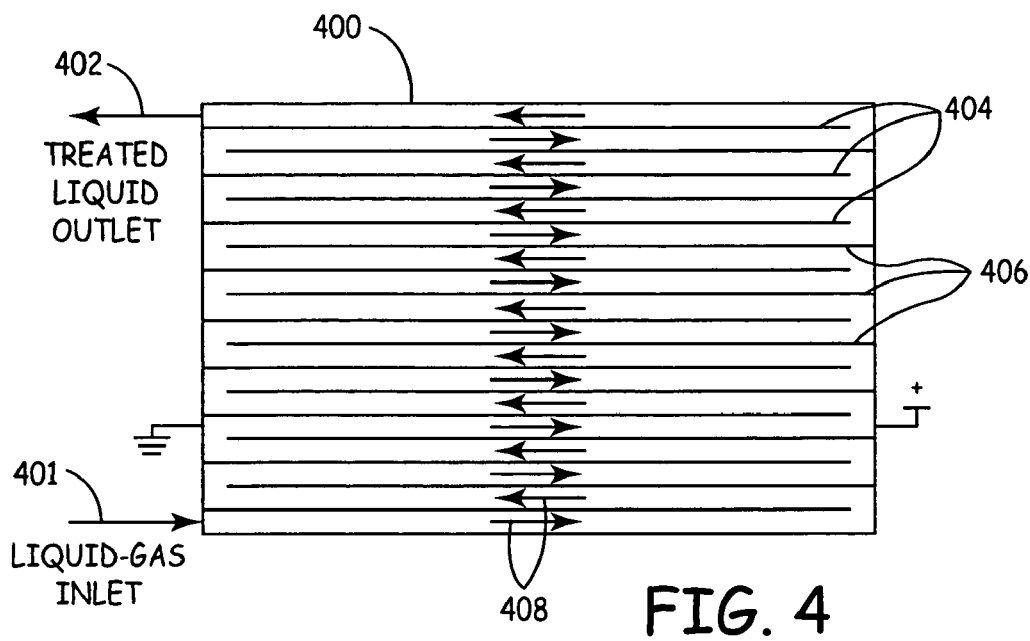
FIG. 4 is a diagram, which schematically illustrates a cross-sectional view of a non-thermal plasma reactor, which has a winding, serpentine flow path, according to one embodiment of the present invention.

FIG. 4 is a diagram, which schematically illustrates a cross-sectional view of a non-thermal plasma reactor which has a winding, serpentine flow path and can be used for reactor 208 (shown in FIG. 2) according to one embodiment of the present invention. Reactor 400 includes a liquid-gas inlet 401, a treated liquid-gas outlet 402 and a plurality of oppositely polarized non-thermal plasma electrodes 404 and 406 which are arranged to form a serpentine liquid flow path indicated by arrows 408. As described above, each electrode 404 and 406 is physically and electrically isolated from the liquid flow path by a respective dielectric barrier. In one embodiment, electrodes 404 and 406 are each formed as a planar electrode panel that is parallel to and separated from the other electrode panels. Each electrode panel 404 and 406 has a polarity that is opposite to the polarity of the next adjacent electrode panel. This creates a plurality of reaction volumes, which are coupled together in series to form flow path 408. Each reaction volume is defined by the gap between a respective pair of electrodes 404 and 406. The serpentine flow path can be used to increase the liquid residence time within reactor 400 and to increase the turbulence of the liquid flow, which may assist in keeping the gas bubbles more evenly distributed and of a small size in the liquid. Any number of reaction volumes can be used in alternative embodiments. For example, reactor 400 can include a single reaction volume such as shown in FIG. 1, two reaction volumes that form a U-shaped flow path, or a plurality of reaction volumes as shown in FIG. 4. In an alternative embodiment, the individual reaction volumes extend parallel to one another from inlet 401 to outlet 402.

Figure 5:
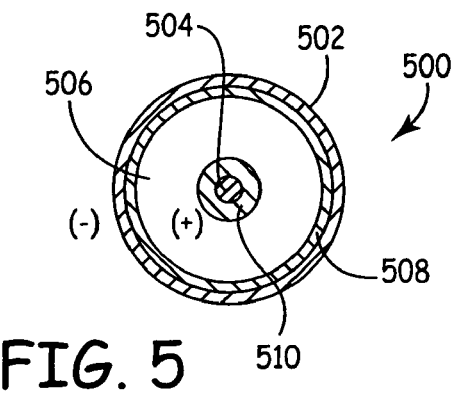
FIG. 5 is a cross-sectional view of a tubular non-thermal plasma reactor according to an alternative embodiment of the present invention.

FIG. 5 is a cross-sectional view of a tubular non-thermal plasma reactor 500 according to an alternative embodiment of the present invention. Reactor 500 has a tubular structure, with flow going into or out of the page in FIG. 5. Reactor 500 includes a tubular ground electrode 502 and a wire high voltage electrode 504, which is coaxial with electrode 502. In an alternative embodiment, electrode 502 is a high voltage electrode and electrode 504 is a ground electrode. Electrodes 502 and 504 are separated by a gap, which defines a reaction volume 506. Electrodes 502 and 504 are physically and electrically isolated from reaction volume 506 by respective dielectric barriers 508 and 510. Dielectric barriers 508 and 510 prevent electrodes 502 and 504 from contaminating the liquid being treated and provide electrical isolation that prevents the liquid within reaction volume 506 from shorting electrode 502 to electrode 504.

Figure 6:
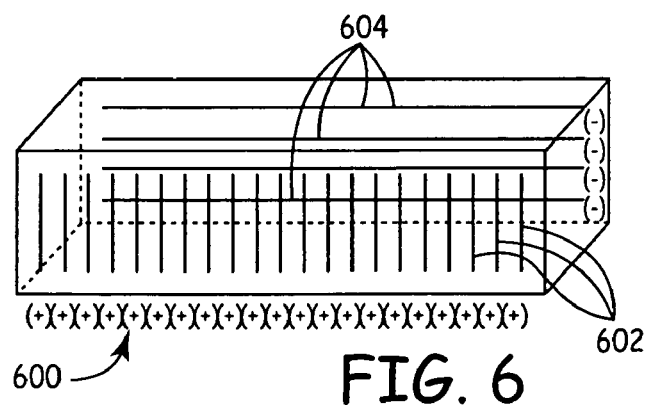
FIG. 6 is a perspective view of a non-thermal plasma reactor having narrow strip electrodes.

FIG. 6 is a perspective, schematic view of a non-thermal plasma reactor 600 having narrow strip electrodes 602 and 604. Electrodes 602 are biased at one polarity, and electrodes 604 are biased at an opposite polarity. Electrode strips 602 and 604 are arranged perpendicular to one another and are spaced about a reaction volume. Each individual electrode 602 and 604 is insulated by a dielectric barrier. For example, all of the electrodes 602 can be embedded within one sheet of dielectric material, and all of the electrodes 604 can be embedded within another sheet of dielectric material. With this type of electrode structure, the local electric fields around electrodes 602 and 604 are greatly enhanced, which ensures discharge takes place easily and effectively in the gas bubbles.

Figure 7A:
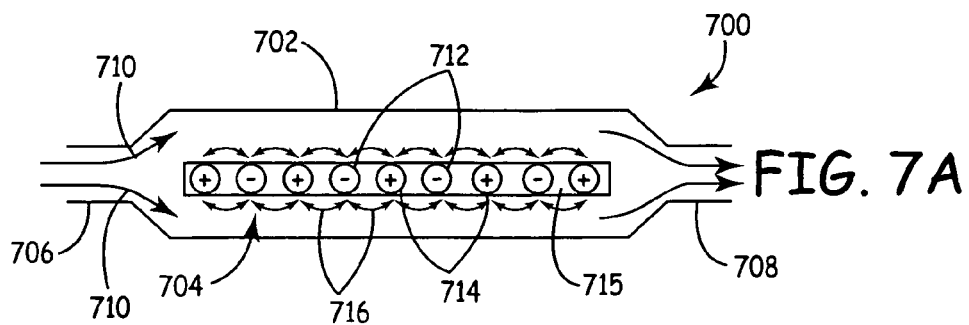
FIG. 7A is a side plan view of a surface discharge-type non-thermal plasma reactor according to another alternative embodiment of the present invention.

FIG. 7A is a side cross-sectional view of a non-thermal plasma reactor 700 according to another alternative embodiment of the present invention. Reactor 700 includes a housing 702 and at least one "surface" discharge electrode 704. Housing 702 has a liquid inlet 706, a liquid outlet 708 and a pair of flow paths 710 extending on either side of surface discharge electrode 704. Surface discharge electrode 704 includes a plurality of adjacent conductors 712 and 714 having opposite polarity. Conductors 712 and 714 are electrically insulated from flow paths 710 by a dielectric material 715. In one embodiment, conductors 712 and 714 are each individually coated with a dielectric material that forms an electrically insulating sheath. In an alternative embodiment, conductors 712 and 714 are embedded in a dielectric material to form an electrode sheet. Conductors 712 and 714 can have diameters of about 0.1 to about 3.0 millimeters, for example, and are each separated by a gap in the range of 0 to 6 millimeters, for example.

Figure 7B:
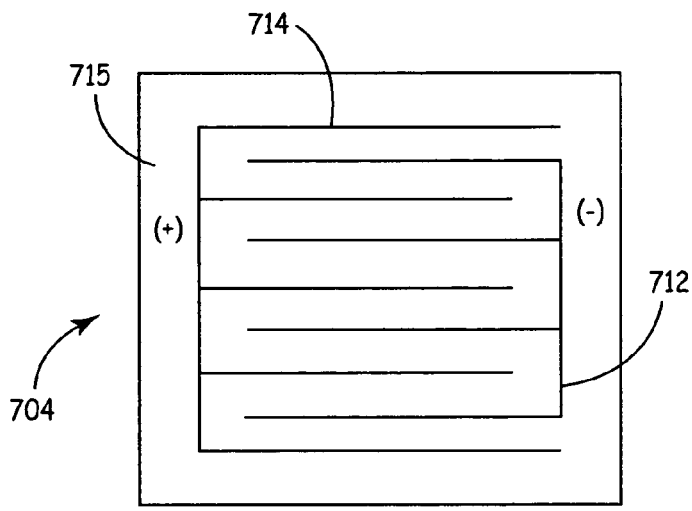
FIG. 7B is a plan view of a surface discharge electrode used in the reactor shown in FIG. 7A.

Excitation of conductors 712 and 714 generates microcurrent electric field discharge paths 716 along the surfaces of electrode 704. Electric field discharge through discharge paths 716 generates non-thermal surface plasma species within the liquid being treated, along the surface of electrode 704. These non-thermal surface plasma species are highly reactive and destroy pathogens living in the liquid, similar to the embodiments discussed above. Electrode 704 can have a variety of shapes, such as planar or tubular. FIG. 7B is a plan view of electrode 704 in planar form, which illustrates one possible arrangement of conductors 712 and 714.

Figure 8:
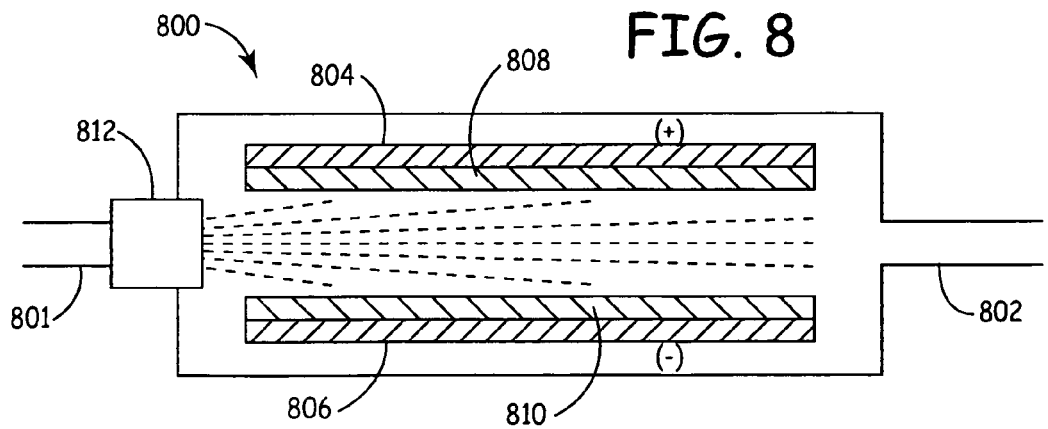
FIG. 8 is a side view of a non-thermal plasma reactor in which the liquid is sprayed into the reaction volume, according to another alternative embodiment of the present invention.

FIG. 8 is a side view of a non-thermal plasma reactor 800 according to another alternative embodiment of the present invention. Reactor 800 includes fluid inlet 801, fluid outlet 802, electrodes 804 and 806 and dielectric barriers 808 and 810. Electrodes 804 and 806 are separated from one another by a gap, which defines a reaction volume between dielectric barriers 808 and 810. Reactor 800 further includes a sprayer 812, which is coupled to fluid inlet 801 for receiving the liquid to be treated. Sprayer 812 spays the liquid through the reaction volume, between dielectric barriers 808 and 810 to form a fine mist within the reaction volume. The treated liquid then exits through liquid outlet 802. Sprayer 812 assists in generating a gas-liquid mixture within the reaction volume, which helps the non-thermal plasma in destroying pathogens living in the liquid.

Figure 9:
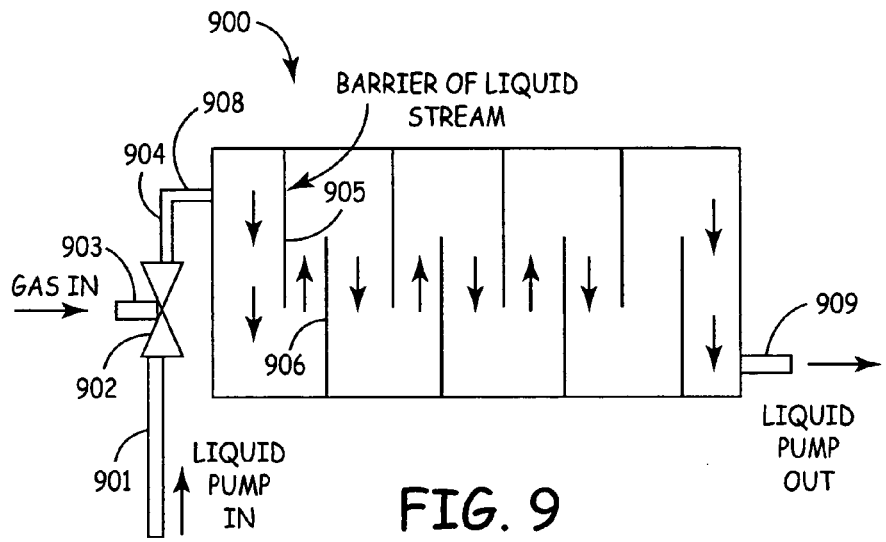
FIG. 9 illustrates a non-thermal plasma reactor having a set of barriers used to increase back pressure within the liquid being treated.

FIG. 9 illustrates an NTP reactor 900 having a set of barriers used to increase the back pressure within the liquid being treated. Briefly referring back to FIG. 2, the stream of the gas-liquid mixture from gas mixing device 206 to reactor 208 is of high speed and high pressure. To some extent, the distribution of gas bubbles in the liquid depends on the back pressure of the mixture. The higher the back pressure, the higher the solubility of the gas in the liquid. In one embodiment, a large tank 202 can be used to increase the back pressure in the system.

In the embodiment shown in FIG. 9, the arrangement of electrode panels is used to increase the back pressure. As liquid is pumped through tube 901, gas injector 902 draws gas into gas inlet 903 and produces a gas-liquid mixture at the outlet of the injector. Tube 904 delivers the gas-liquid mixture from gas injector 902 to inlet 908 of NTP reactor 900. NTP reactor 900 has a plurality of electrode plates 905 and 906, which are arranged to form a serpentine flow path from inlet 908 to outlet 909 and are arranged perpendicular to inlet 908. With this arrangement, electrode plates 905 and 906 form barriers to the liquid stream entering from inlet 908 and being passed from one portion of the flow path to the next. These barriers further increase back pressure within the gas-liquid mixture.

Figure 10:
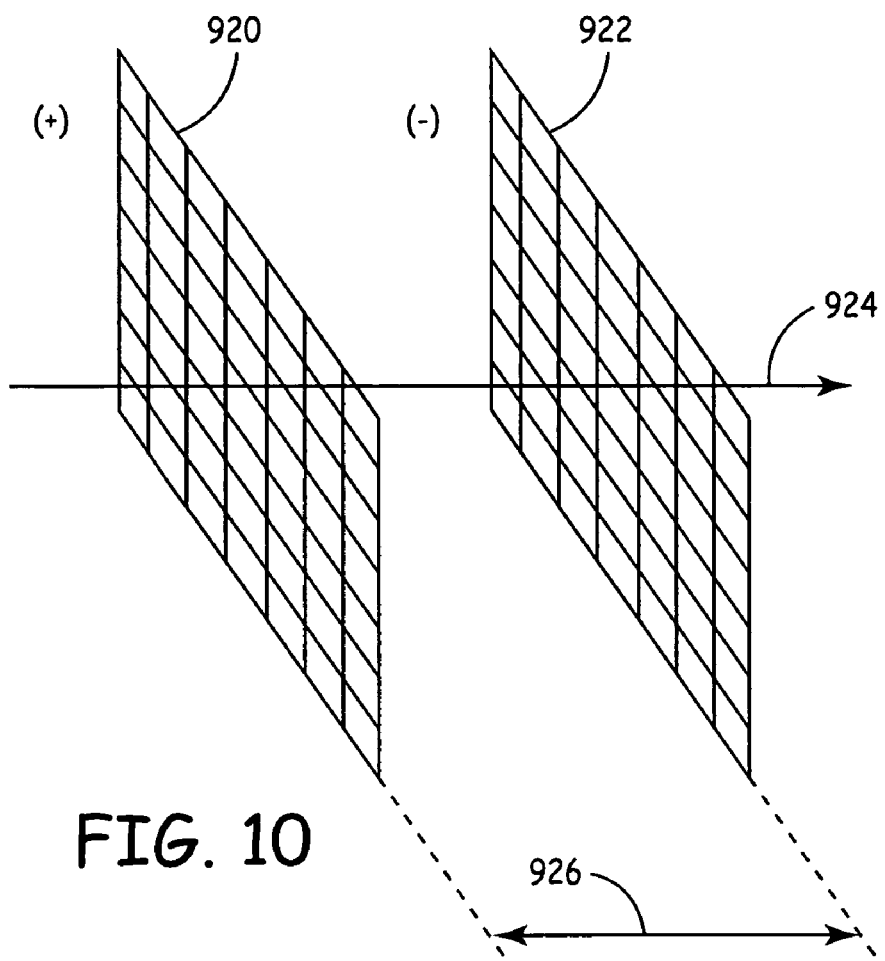
FIG. 10 is a simplified, perspective view of two mesh-type non-thermal plasma electrodes that can be used for disinfecting liquids according to another alternative embodiment of the present invention.

FIG. 10 is a simplified, perspective view of two mesh-type non-thermal plasma electrodes 920 and 922 that can be used for pasteurizing liquids according to another alternative embodiment of the present invention. Electrodes 920 and 922 are each formed of a conductive wire mesh, which has been coated with a dielectric material such that the wire mesh is electrically insulated from the liquid being treated. The dielectric coating is formed so that the area between each conductive segment in the mesh is open to fluid flow. Any coating technique can be used, such as physical vapor deposition (PVD) or chemical vapor deposition (CVD).

The liquid to be treated is passed through electrodes 920 and 922 in the direction of arrow 924, substantially perpendicular to the planes formed by electrodes 920 and 922. As the liquid passes through meshes 920 and 922, electrodes 920 and 922 are electrically coupled to opposite voltage potentials, which creates a non-thermal plasma within gap 926 for treating the liquid present within the gap. If the openings in electrodes 920 and 922 are sufficiently small, the openings can further assist in breaking-up larger gas bubbles and maintaining the gas bubbles in the liquid at a sufficiently small size. Other arrangements can also be used, and meshes 920 and 922 can be non-planar. Also, a series of electrode pairs 920 and 922 can be used, wherein the liquid flows sequentially through each electrode pair for treatment. In an alternative embodiment, a gas injector or diffuser is not used to mix the gas and liquid. Rather, the gas is supplied through a tube into the reactor and is then broken into small bubbles as the gas and liquid are forced through the small openings in the mesh electrodes.

1. Experimental Results

Several experiments were performed to demonstrate the effectiveness of non-thermal plasma in reducing pathogens living in a biological fluid.

Figure 11:
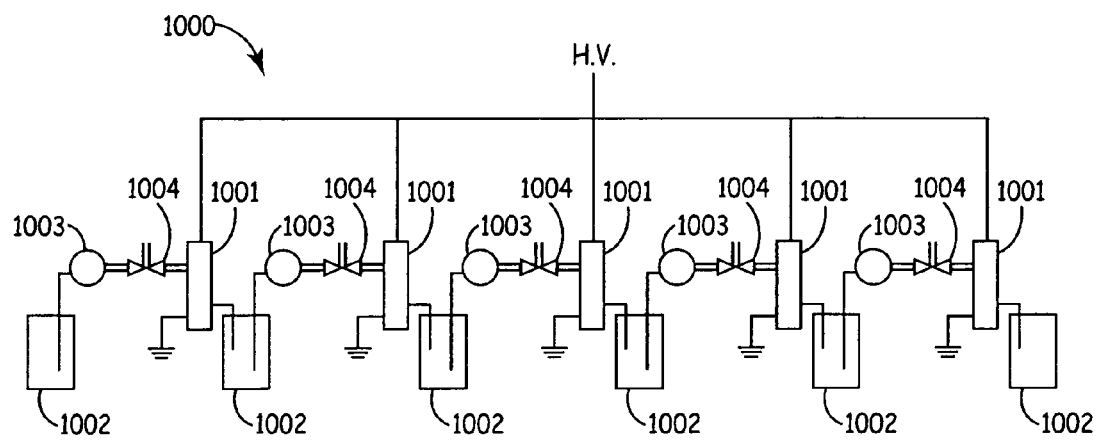
FIG. 11 is a diagram of a disinfection system having five NTP reactors connected together in series.

For example, the NTP pasteurization system shown in FIG. 11 was built and used to treat fresh cow blood samples. System 1000 included five NTP reactors 1001 connected together in series with each NTP reactor 1001 having its own source tank 1002, pump 1003 and gas injector 1004. The outlet of each NTP reactor 1001 was coupled to the source tank 1002 of the next reactor 1001 in the series. The plurality of gas injectors 1004 ensured that the gas-liquid mixture contained sufficiently fine bubbles throughout the flow. Air was injected through each injector 1004 at 2 cubic feet per hour (CFH). Pumps 1003 pumped the liquid through system 1000 at 30 gallons per hour. The electrical connections to the NTP reactors 1001 were coupled together in parallel with one another and were excited at 20–30 kV alternating-current (AC) voltage.

Each reactor 1001 had a similar structure as that described with reference to FIG. 4, but with only two individual reaction volumes coupled in series with one another to form a serpentine flow path. Each electrode panel was formed of a thin, flat solid copper plate, which was attached to the backside of an epoxy resin board such that the copper plate was physically isolated from the liquid being treated. The epoxy resin board served as a dielectric layer, which had a thickness of 1.5 millimeters. The discharge gap between the dielectric layers, across the reaction volume, was 7 millimeters. The effective discharge volume for each leg of the serpentine flow path was 500 millimeters by 10 millimeters by 7 millimeters. These parameters were used as examples only and can be further modified or optimized for treating a particular biological fluid in a particular manner with one or more NTP reactors for a particular gas, such as oxygen.

Each test was conducted with a one liter cow blood sample that was inoculated with more than five logs of either *Escherichia coli* or *Salmonella*. The tests were conducted under three conditions: (1) without gas injection; (2) with air injection; and (3) with oxygen injection. The output from each stage was sampled at source tanks 1002 to verify the reduction of bacteria at different stages of the system.

a. Inactivation of *Escherichia coli* and *Salmonella*

Figure 12:
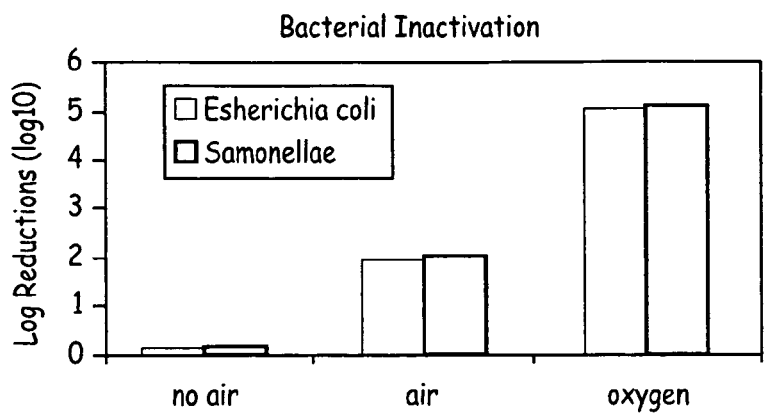
FIG. 12 is a graph showing the level of inactivation of *Escherichia coli* and Salmonella in cow blood samples.

FIG. 12 shows the level of inactivation of *Escherichia coli* and *Salmonella* in the blood samples. The test results in FIG. 12 show that NTP treatment can cause five logs of *Escherichia coli* and *Salmonella* reduction under the condition outlined above. No difference in bacterial inactivation was found between *Escherichia coli* and *Salmonella*. Oxygen as a mixture gas media in biological fluids was more effective than air. One possible explanation is that air has more nitrogen, which requires higher ionization energy than oxygen, and therefore the concentration of energetic radicals in non-thermal plasma would be lower in air than in oxygen.

b. Change in Hematological Properties of Blood Samples

Blood is regarded as one of the most delicate biological fluids. Hematology and morphology studies were also performed on the samples to verify that non-thermal plasma treatment does not cause significant changes in the biologically active ingredients in blood. These studies included tests on blood specifications of hematology, such as morphology, blood cell count, blood plasma hemoglobin, and coagulation profile, the results of which are shown in FIGS. 13–17. The morphology of blood cells remained normal after treatment.

Figure 13:
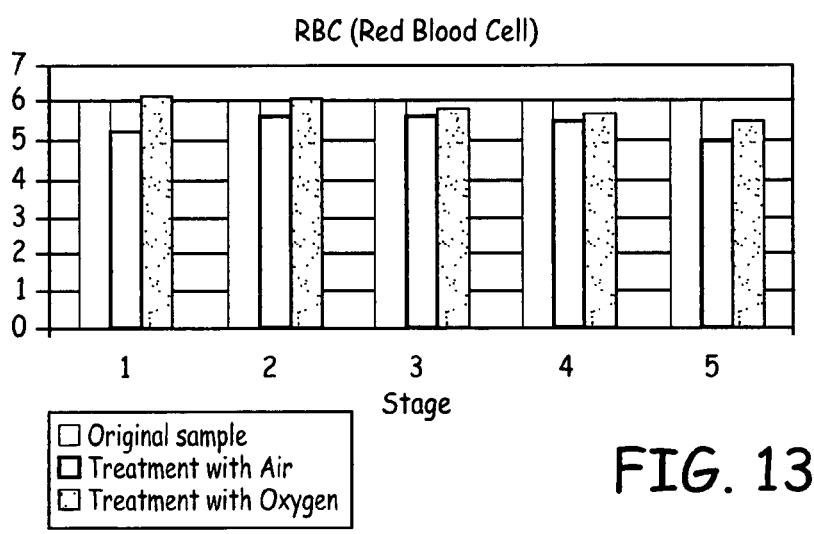
FIG. 13 is a graph illustrating red blood cell count as a function of the number of NTP stages in and NTP system and the type of injected gas (air or oxygen).
Figure 14:
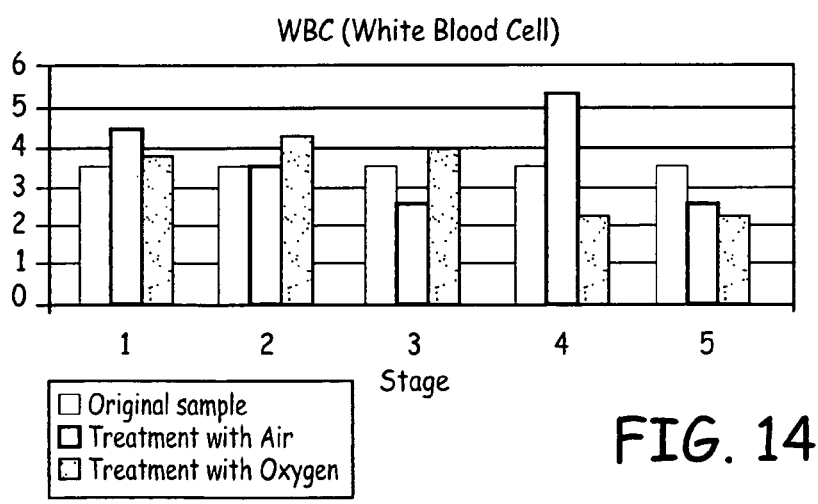
FIG. 14 is a graph illustrating white blood cell count as a function of the number of NTP stages in the system and the type of injected gas (air or oxygen).

FIG. 13 is a graph illustrating the red blood cell count as a function of the number of NTP stages in the system and the type of injected gas (air or oxygen). FIG. 14 is a graph illustrating the white blood cell count as a function of the number of NTP stages in the system and the type of injected gas (air or oxygen). From FIGS. 13 and 14, it is seen that red blood cell count and white blood cell count did not change significantly. The small variations noticed in the test results may be caused by statistical error and the non-uniform distribution of blood cells.

Figure 15:
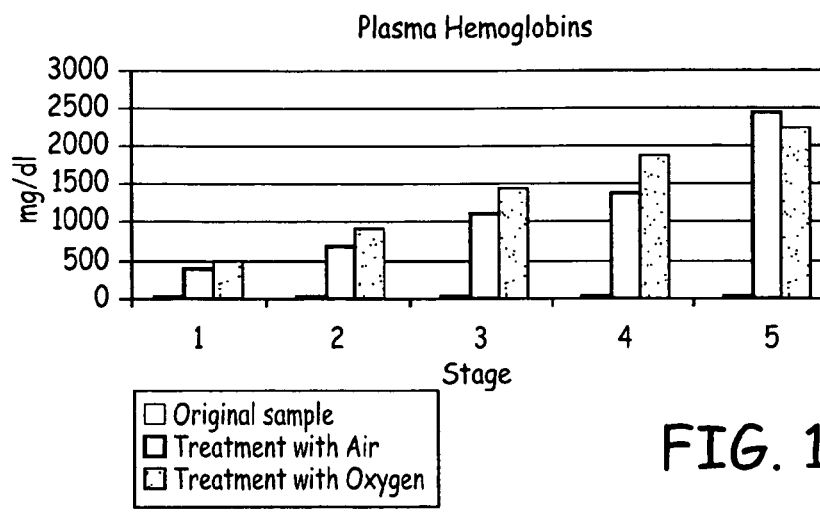
FIG. 15 is a graph illustrating plasma hemoglobin in milligrams per deciliter (mg/dl) as a function of the number of NTP stages in the system and the type of injected gas (air or oxygen).

FIG. 15 is a graph illustrating blood plasma hemoglobin in milligrams per deciliter (mg/dl) as a function of the number of NTP stages in the system and the type of injected gas (air or oxygen). The blood plasma hemoglobin increased after treatment. Although the hemoglobin increased after treatment, the blood plasma activated partial thromboplastin time (APTT) and fibrinogen showed no significant difference before and after treatment as shown in FIGS. 16 and 17.

Figure 16:
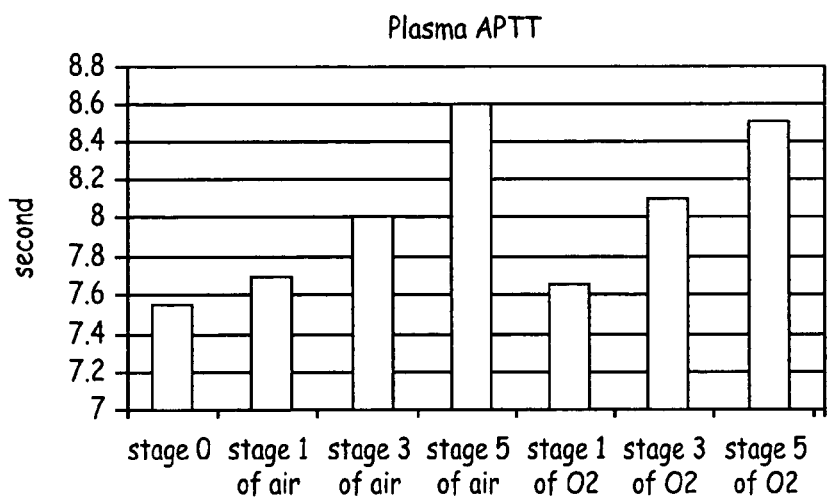
FIG. 16 is a graph illustrating plasma APTT in seconds as a function of the number of NTP stages in the system and the type of injected gas (air or oxygen).

FIG. 16 is a graph illustrating blood plasma APTT in seconds as a function of the number of NTP stages in the system and the type of injected gas (air or oxygen). Normal APTT for a cow is 6.8 to 9.2 seconds. The test on blood plasma APTT varied from 7.5–8.6 after NTP treatment. They are within the normal range of 6.8 to 9.2 seconds for ATPP in a cow.

Figure 17:
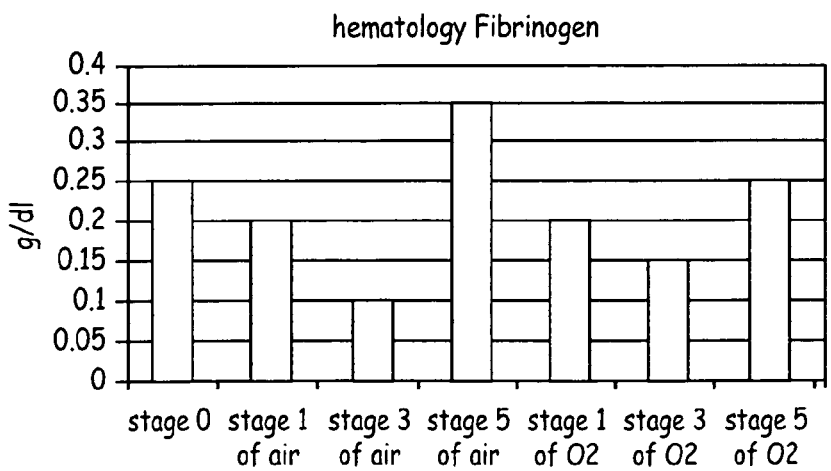
FIG. 17 is a graph illustrating hematology fibrinogen in grams per deciliter (g/dl) as a function of the number of NTP stages in the system and the type of injected gas (air or oxygen).

FIG. 17 is a graph illustrating hematology fibrinogen in grams per deciliter (g/dl) as a function of the number of NTP stages in the system and the type of injected gas (air or oxygen). The hematology fibrinogen values varied from 0.1–0.35 g/dl as a result of NTP treatment, which are also within a normal range of 0.1–0.7 g/dl for cow blood.

The conclusions from the above-experiments are that a five-log reduction of bacteria (*Escherichia coli* and *Salmonellae*) inoculated in cow blood can be achieved using the NTP system of FIG. 11, and the NTP treatments do not cause significant changes in blood hematology and morphology. Red and white blood cell counts do not change significantly. While the blood plasma hemoglobin increases after treatment, the values of blood plasma fibrinogen and APTT remain within normal ranges after treatment.

2. Coagulation of Blood and Self-cleaning of NTP System

Coagulation of biological fluids is a normal phenomenon. After a specified period of use or after a particular treatment or set of treatments, the NTP system should be cleaned to deodorize the NTP system and to prevent different types of biological fluid samples treated by the same system from contaminating each other (i.e., cross contamination). The NTP system shown in FIG. 11 and the systems of various other embodiments of the present invention lend themselves well to cleaning. The system can be flushed with sterile water to prevent a biological film from forming on the contacting surfaces of the system. During the water cleaning/flushing process, NTP system can be electrically operated to produce ozone and ozonated water within the system which aid in cleaning the reactors, pipes, pumps, etc. in the system. The ozone-aided self-cleaning process has been found to be very effective in cleaning and deodorizing the NTP system and in preventing cross contamination. The entire process of cleaning such blood-circulating apparatus is well-known in the art, having been practiced for many years for hemodialysis. The present invention utilizes the same principles and methods of between-use disinfection.

Also, the contacting surfaces of the system, such as the electrode surfaces, can be covered with a thin film coating to reduce biological fluid coagulation and biological film formation. Any biologically-safe low-friction coating can be used, such as polytetrafluoroethylene (PTFE) which is available under the tradename TEFLON from E. I. du Pont de Nemours and Company.

3. Separation of Gas From Blood or Other Biological Fluids

As discussed above, gas injection into the biological fluids being treated is helpful in inducing non-thermal plasma species that react with the pathogenic microorganisms within the fluids. It was shown that the injected gas, especially oxygen, is a helpful agent in promoting bacterial inactivation (See FIG. 12). Following NTP treatment it is often desirable for the injected gas to be separated from the treated biological fluid. The gas can be separated with a gas separator.

Figure 18:
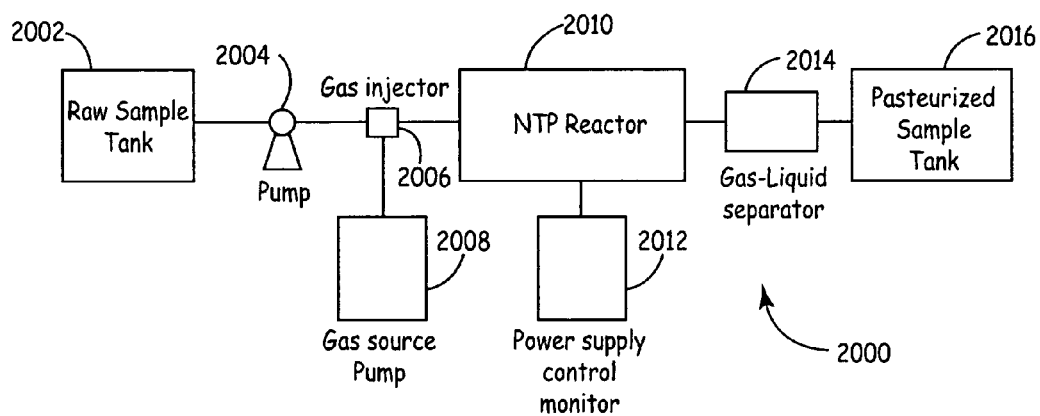
FIG. 18 is a block diagram illustrating an NTP system having a gas-liquid separator according to one embodiment of the present invention.

FIG. 18 is a block diagram illustrating an NTP system 2000 having a gas separator according to one embodiment of the present invention. NTP system 2000 includes a raw sample receiving tank 2002, a pump 2004, a gas injector 2006, a gas source pump 2008, an NTP reactor 2010, a power supply and temperature monitor 2012, gas-liquid separator 2014, and pasteurized sample tank 2016. In one embodiment, gas source pump 2008 can include an oxygen generator, for example. Gas separator 2014 can include any suitable liquid/gas separator, and can include a vacuum source if desired for assisting in the removal of gas from the liquid. These small separators are quite common, particularly in the fuel cell industry, where it is necessary to remove carbon dioxide from the electrolyte fluids, or in bioreactors for fermentation. They operate in a variety of ways, depending on the reliability level required: gravity (gas bubbles consolidate and rise to the top), centrifuge, and pressurized types (where a reduction in fluid pressure causes gas bubbles to rise rapidly). A common design is the VIG porous Teflon™ membrane separator for the environmental treatment industry, which uses a filter that will pass only gas through it, leaving the liquid behind. Yokota manufactures a "de-foaming pump" that utilizes a combination of centrifugal and pressure forces to continuously remove high volumes of bubbles from liquid.

4. Alternative Reactor Embodiments

Figure 19:
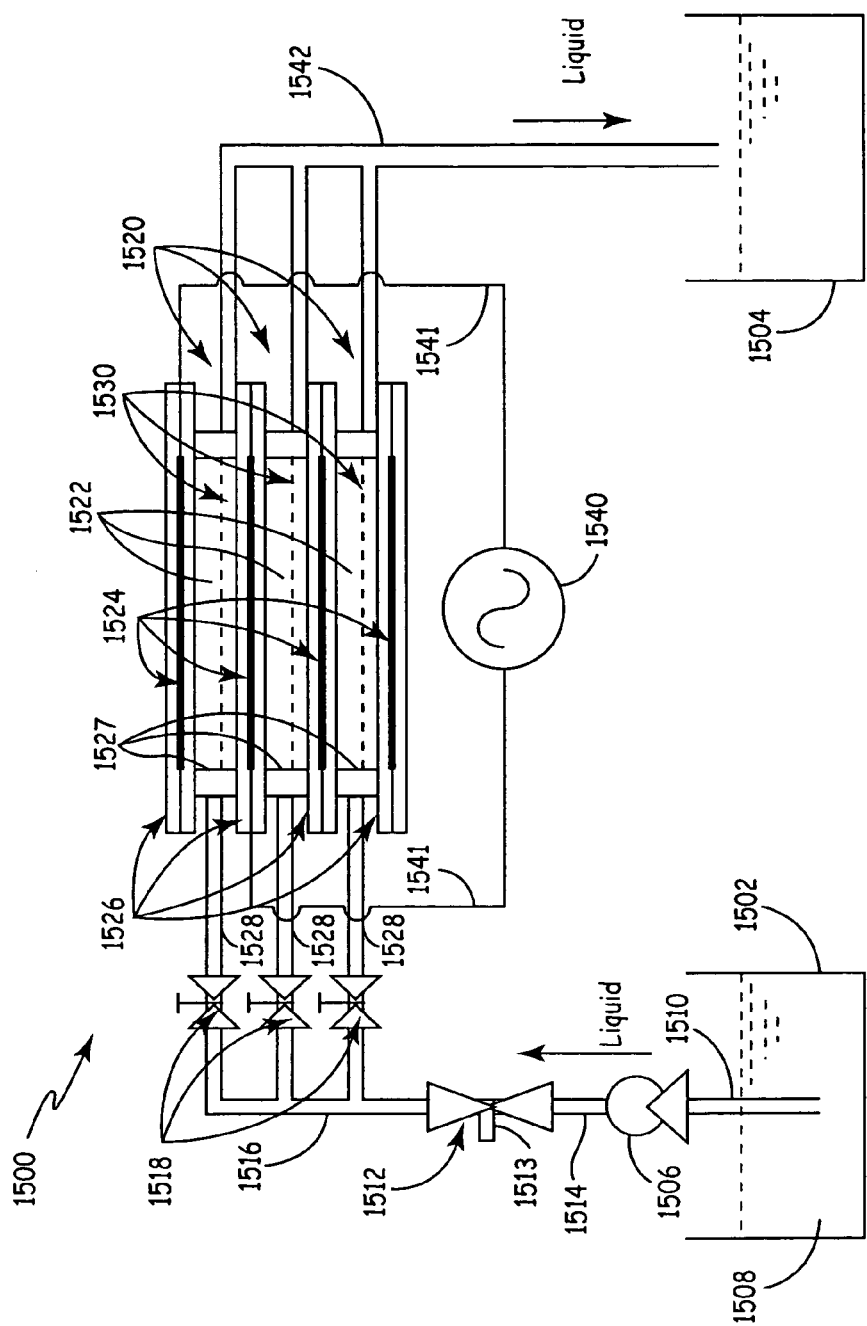
FIG. 19 is a diagram, which schematically illustrates a multiple-plate non-thermal plasma reactor according to another embodiment of the present invention.

FIG. 19 is a diagram, which schematically illustrates a multiple-plate non-thermal plasma reactor 1500 according to another embodiment of the present invention. Reactor 1500 has a liquid source tank 1502 and a liquid outlet tank 1504. Pump 1506 draws liquid 1508 from tank 1502 through tube 1510 and supplies the liquid to gas injector 1512 through tube 1514. As liquid 1508 is pumped through gas injector 1512, gas injector 1512 draws gas into gas inlet 1513 and produces a gas-liquid mixture at the outlet of the injector. Tube 1516 delivers the gas-liquid mixture to valves 1518, which control flow to a plurality of parallel NTP reactor cells 1520. The term "tube" as used in the specification and claims can include any conduit or passage formed of any suitable material and having any suitable cross-sectional shape.

Each cell 1520 has a reaction volume 1522 and a par of oppositely polarized electrodes 1524, which are electrically and physically isolated from the reaction volume by dielectric barriers 1526. Tubes 1528 deliver the gas-liquid mixture to reaction volumes 1522 for treatment. Dashed lines 1530 represent the upper surfaces of the gas-liquid mixtures in each reaction volume. Spacers 1527 define the height of reaction volumes 1522, between opposing surfaces of dielectric barriers 1526.

High voltage power supply 1540 delivers electrical excitation energy to electrodes 1524 through conductors 1541 for generating non-thermal plasma within reaction volumes 1522. In one embodiment, power supply 1540 delivers an AC voltage of 5 kV to 30 kV at a frequency of 1 Hz to 1000 Hz, for example. Other voltages and frequencies can also be used. The treated gas-liquid mixture 1530 is then returned to tank 1504 through tubes 1542. Electrodes 1524 and dielectric barriers 1526 can have any structure and gap size, such as those disclosed in the present application. Any number of parallel NTP reactor cells 1520 can be used in alternative embodiments of the present invention.

Figure 20:
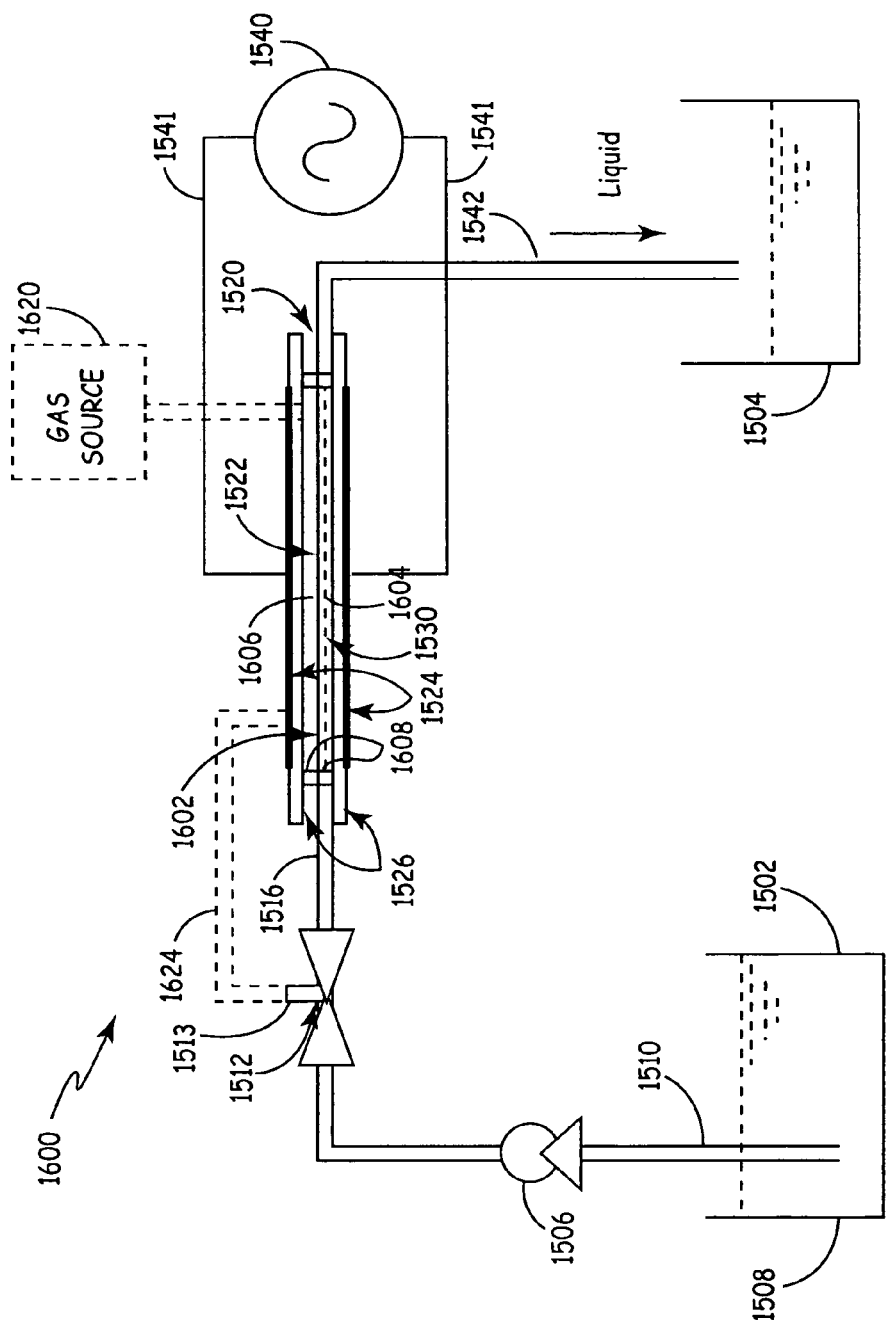
FIG. 20 is a diagram that schematically illustrates a two-dielectric barrier NTP reactor having a discharge initiation region according to another alternative embodiment of the present invention.

FIG. 20 is a diagram that schematically illustrates a two-dielectric barrier NTP reactor 1600 having a discharge initiation region according to another alternative embodiment of the present invention. The same reference numerals are used in FIG. 20 as were used in FIG. 19 for the same or similar elements. In this embodiment, a film or plate 1602 divides reaction volume 1522 into a treatment region 1604 and a discharge initiation region 1606. Film 1602 is suspended in the space between dielectric plates 1526 by spacers 1608, for example. Tube 1516 delivers the gas-liquid mixture 1530 into treatment region 1604, and tube 1542 returns the treated gas-liquid mixture to tank 1504. Film 1602 contains gas-liquid mixture 1530 in treatment region 1604 and prevents the gas-liquid mixture from entering into discharge initiation region 1606. Discharge initiation region 1606 can be filled with various gases, such as air, another gas or a gas mixture. Discharge initiation region 1606 can also be substantially void of any gas and held under a vacuum at below-normal atmospheric pressure. In this embodiment, electrodes 1524 are parallel plates, and discharge initiation region 1606 and treatment region 1604 are rectangular volumes.

In one embodiment, film 1602 is formed of a dielectric material, such as a transparent membrane of polytetrafluoroethylene from E. I. du Pont de Nemours and Company. In alternative embodiments, film 1602 can be formed of a transparent epoxy resin or other types of film or sheet materials. Film 1602 has good dielectric properties and allows one or more of the non-thermal plasma species to pass from discharge initiation region 1606 to treatment region 1604. However, film 1602 should not allow the gas-liquid mixture 1530 to pass into discharge initiation region 1606. Film 1602 can also be non-dielectric, as long as there is at least one other dielectric barrier between electrodes 1524. Film 1602 can also include an ion-selective membrane. In one embodiment, film 1602 is made as thin as possible and transparent so as to limit absorption or reflection of the non-thermal plasma species passing through to treatment region 1604. For example, film 1602 can have a thickness between 0.02 millimeters to 1 millimeter. Smaller or larger thicknesses can also be used. The surfaces of film 1602 can be hydrophilic or hydrophobic. Examples of commercially available films that are effective include CS Hyde 56-10—a Teflon coated fabric that is 10 mils thick and is tan in color, TetraTex Pourous PTFE—a PTFE membrane that is white in color, and a Spetrum Lab filter disk—a 70 mm diameter Teflon mesh filter media that is semi-translucent. Other films can also be used.

During operation, electrodes 1524 are energized. The resulting electrical field between the electrodes generates non-thermal plasma species within regions 1604 and 1606. Non-thermal plasma species within region 1606 are easily generated, and the discharge across region 1606 is fairly uniform. This assists in generating more consistent and uniform non-thermal plasma species within treatment region 1604. Without discharge initiation region 1606, it has been found that the discharge within the gas-liquid mixture 1530 can be inconsistent or non-uniform, depending on the particular apparatus. The NTP species generated within initiation region 1606 that pass into treatment region 1604 react with the gas-liquid mixture to kill more evenly and consistently pathogens living in the liquid. Film 1602 also protects the upper electrode 1524 and the upper dielectric barrier 1526 from contamination or staining by gas-liquid mixture 1530.

In addition, the discharge initiation region 1606 can be used to limit the generation of ozone more easily in applications where ozone is not desired. This region can be filled with a gas other than air, such as nitrogen, carbon dioxide or another gas, and still provide an effective treatment of any live pathogens in the liquid. In these embodiments, gas injector 1512 can be used to inject a gas other than air to further limit the generation of ozone. However, air can also be used if desired. Discharge initiation region 1606 can also be held under a small vacuum to further limit the amount of gas in the region and therefore the amount of ozone that is generated.

In an alternative embodiment, NTP reactor 1600 further includes a gas source 1620, which supplies gas to discharge initiation region 1606 through tube 1622. In addition, a tube 1624 can by coupled between discharge initiation region 1606 and gas inlet 1513 of gas injector 1512. During operation, gas injector 1512 draws gas containing the non-thermal plasma species from initiation region 1606 into gas inlet 1513 to further enhance the mixture of non-thermal plasma species in the liquid being treated. Gas source 1620 replaces the gas drawn out of discharge initiation region 1606. In another embodiment the NTP species generated in region 1606 is mixed with the gas-liquid mixture 1530 at the outlet of NTP cell 1520. Mixing can be accomplished through a gas injector similar to injector 1512, a diffuser or any other apparatus or method that forces or assists in the NTP species passing through or contacting the treated liquid.

In a further embodiment (not shown in FIG. 20), a second dielectric film 1602 is positioned on the other side of treatment region 1604, between treatment region 1604 and bottom dielectric barrier 1526. The second dielectric film can be spaced from the bottom dielectric barrier 1526 by a further discharge initiation region 1606, such that both sides of treatment regions 1604 have a discharge initiation region 1606.

One or more of the dielectric barriers 1526 and 1602 can be eliminated as long as there is at least one dielectric barrier between electrodes 1524. For example, both dielectric barriers 1526 can be eliminated such that dielectric film 1602 serves to separate regions 1604 and 1606 and as the sole dielectric material between electrodes 1524. In yet a further embodiment, dielectric film 1602 is eliminated and one or both of the dielectric barriers 1526 are spaced from their respective electrodes 1524. In this embodiment, the liquid being treated will still have no direct contact with electrodes 1530, and the spaces between dielectric barriers 1526 and their respective electrodes 1524 can be used as discharge initiation regions similar to region 1606. Also, the gas injector can be eliminated in alternative embodiments of reactor 1600 and in alternative embodiments of the reactors shown in the various other figures or discussed herein.

Figure 21:
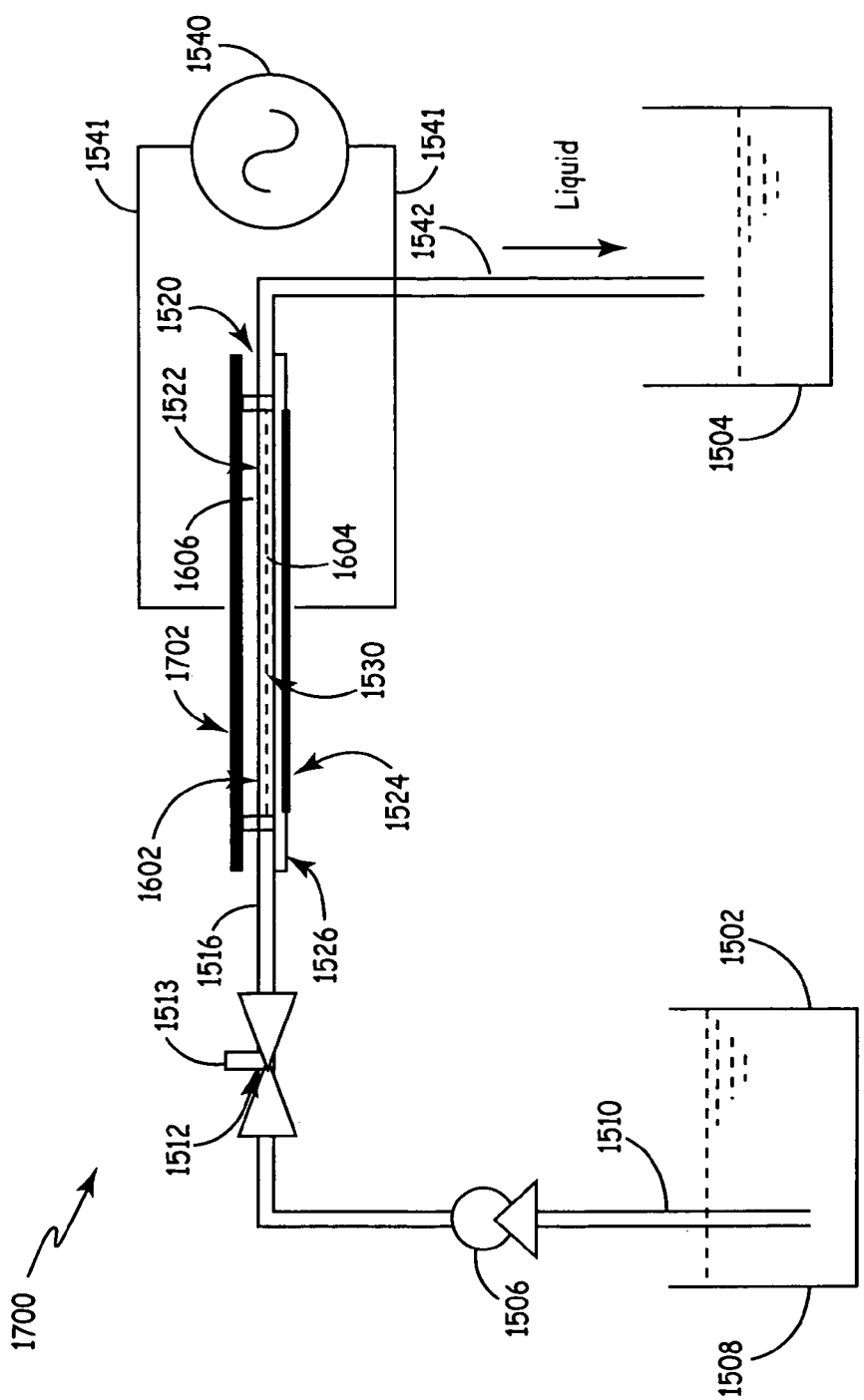
FIG. 21 is a diagram, which illustrates an NTP reactor according to another alternative embodiment of the present invention.

FIG. 21 is a diagram, which illustrates an NTP reactor 1700 according to another alternative embodiment of the present invention. Again, the same reference numerals that are used in FIG. 21 as were used in FIGS. 19–20 for the same or similar elements. In this embodiment NTP cell 1520 has a dielectric film 1602, which separates gas-liquid mixture 1530 from discharge initiation region 1606 and a bare metal electrode 1702. The upper dielectric barrier 1526 (shown in FIG. 20) adjacent the upper electrode 1524 has been removed. In another embodiment, the lower dielectric barrier 1526 can also be removed such that dielectric film 1602 serves as the main dielectric barrier between electrodes 1524.

Figure 22:
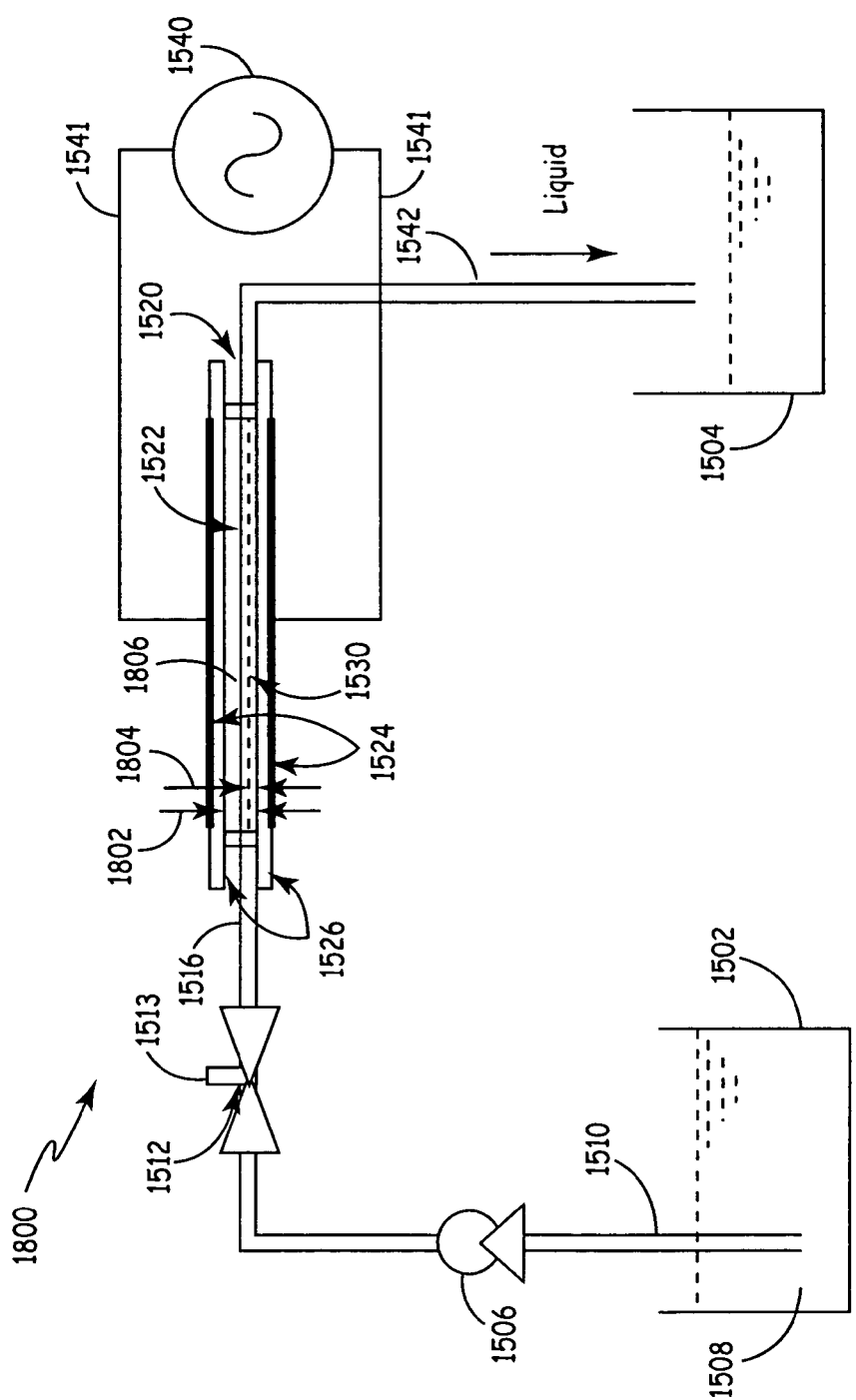
FIG. 22 is a diagram, which schematically illustrates an NTP reactor according to another embodiment of the present invention.

FIG. 22 is a diagram, which schematically illustrates an NTP reactor 1800 according to another embodiment of the present invention. NTP reactor 1800 is similar to NTP reactor 1600 shown in FIG. 20, but has no dielectric film 1602. Reaction volume 1522 has a height 1802 that exceeds the height 1804 of the gas-liquid mixture 1530 flowing through reaction volume 1522 to create a gap 1806 between the upper surface of mixture 1530 and the bottom surface of the upper dielectric barrier 1526. As long as the gap 1806 is maintained during operation, the gap can serve as a discharge initiation region. The gap can be maintained by controlling or otherwise setting the volume flow of gas-liquid mixture 1530 through the inlet and outlet of reaction volume 1522 such that the gas-liquid mixture remains confined to the treatment region. Gap 1806 can be filled with air or any other suitable gas.

Figure 23:
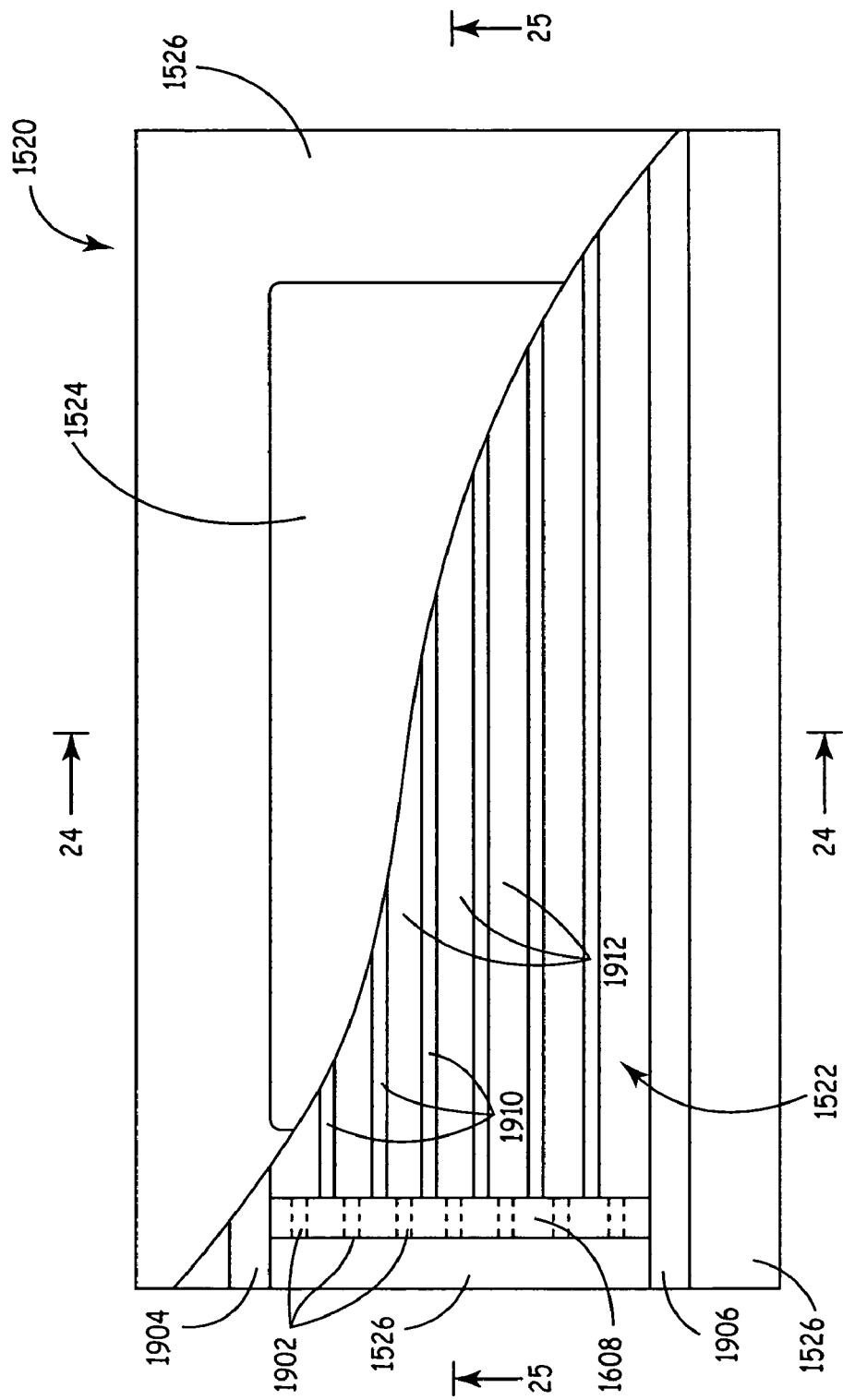
FIG. 23 is a top plan view of one of the NTP cells shown in FIGS. 19–22, according to one embodiment of the present invention.

FIGS. 23–25 show the electrode structure of one of the NTP cells 1520 shown in FIGS. 19–22, according to one embodiment of the present invention. FIG. 23 is a top plan view of the NTP cell 1520 in which upper electrode 1524 and upper dielectric barrier 1526 are partially cut-away to expose a portion of bottom dielectric barrier 1526. FIG. 24 is a cross-sectional view of NTP cell 1520, taken along lines 24—24 of FIG. 23. FIG. 25 is a cross-sectional view of NTP cell 1520 taken along lines 25—25 of FIG. 23.

In FIGS. 23–25, dielectric film 1602 is removed for clarity. A pair of opposing end spacers 1608 and 1609 and opposing sidewall spacers 1906 define the reaction volume between the upper and lower dielectric barriers 1526 and contain the gas-liquid mixture being treated. End spacer 1608 has a plurality of passages 1902 (shown in dashed lines in FIG. 23) for passing the gas-liquid mixture from tube 1516 (shown in FIGS. 19–22) to the reaction volume. End spacer 1609 (FIG. 17) has similar passages 1902 for passing the treated gas-liquid mixture to tubes 1542 (shown in FIGS. 19–22).

Within reaction volume 1522, upper surface of the lower dielectric barrier 1526 can include a plurality of raised ridges or separating walls 1910 that maintain a dispersed flow of the gas-liquid mixture through reaction volume 1522. Separating walls 1910 define a plurality of recessed channels 1912 along which the gas-liquid mixture flows. Separating walls 1910 can have heights that are equal to the height of reaction volume 1522 or less than the height of reaction volume 1522. Spacers 1608, 1904, and 1906 and separating walls 1910 can be formed of the same material as dielectric barrier 1526 or from different material.

Figure 26:
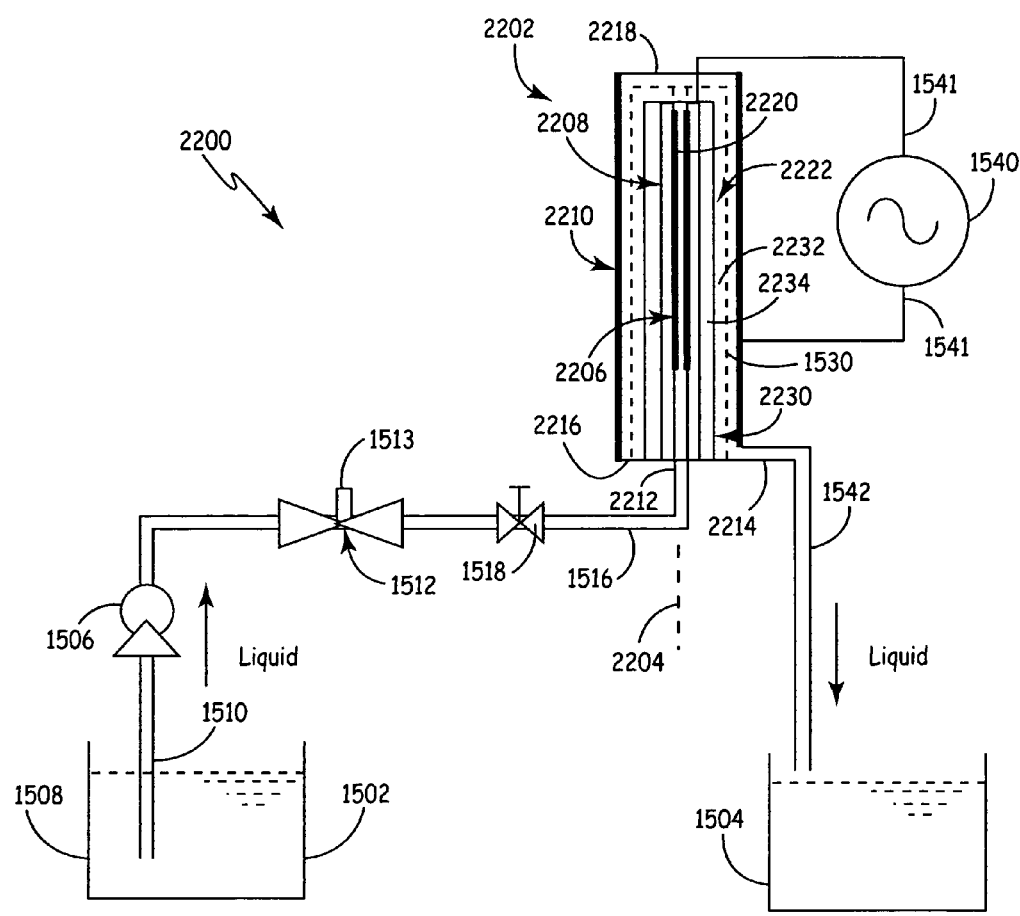
FIG. 26 is a diagram, which schematically illustrates an NTP reactor according to another alternative embodiment of the present invention.

FIG. 26 is a diagram, which schematically illustrates an NTP reactor 2200 according to another alternative embodiment of the present invention. Again, the same reference numerals are used in FIG. 26 as were used in FIGS. 19–25 for the same or similar elements. NTP reactor 2200 has a cylindrical NTP cell 2202 having a central axis 2204, which is oriented normally (i.e., vertically) with respect to the floor on which reactor 2200 is supported and therefore parallel to the gravitational forces of the earth. NTP cell 2202 has a lower end 2216, an upper end 2218, a cylindrical inner stainless steel ground (or alternatively high voltage) electrode 2206, a cylindrical inner dielectric barrier 2208 and a cylindrical outer high voltage (or alternatively ground) electrode 2210. Cell 2202 has an inlet 2212 and an outlet 2214 located at the bottom end 2216 of cell 2202. The space between the outer diameter of dielectric barrier 2208 and the inner diameter of high voltage electrode 2210 forms a reaction volume 2222 within which gas-liquid mixture 1530 is treated.

Tube 1516 is coupled between valve 1518 and inlet 2212. The interior of cylindrical ground electrode 2202 and dielectric barrier 2208 serves as a passageway 2220 for delivering gas-liquid mixture 1530 (shown in dashed lines) to top end 2218 of NTP cell 2202. As gas-liquid mixture 1530 exits the top of passageway 2220, the gas-liquid mixture falls through reaction volume 2222 due to the force of gravity. The treated gas-liquid mixture 1530 then exits outlet 2214 and returns to tank 1504 through tube 1542. The falling gas-liquid mixture 1530 maintains the mixture of gas and liquid and increases the surface area of the liquid that is exposed to the NTP species. This can further increase the effectiveness of the NTP treatment. Alternatively, inlet 2212 can be positioned at upper end 2218.

NTP cell 2202 further includes a cylindrical dielectric film 2230, which separates reaction volume 2222 into a treatment region 2232 and a discharge initiation region 2234. Discharge initiation region 2234 can be filled with a gas or a vacuum, as discussed above, and is physically isolated from the gas-liquid mixture being treated in region 2232. In an alternative embodiment, initiation region 2234 is positioned between treatment region 2232 and electrode 2210. Additional discharge initiation regions can also be used, as discussed above.

Figure 27:
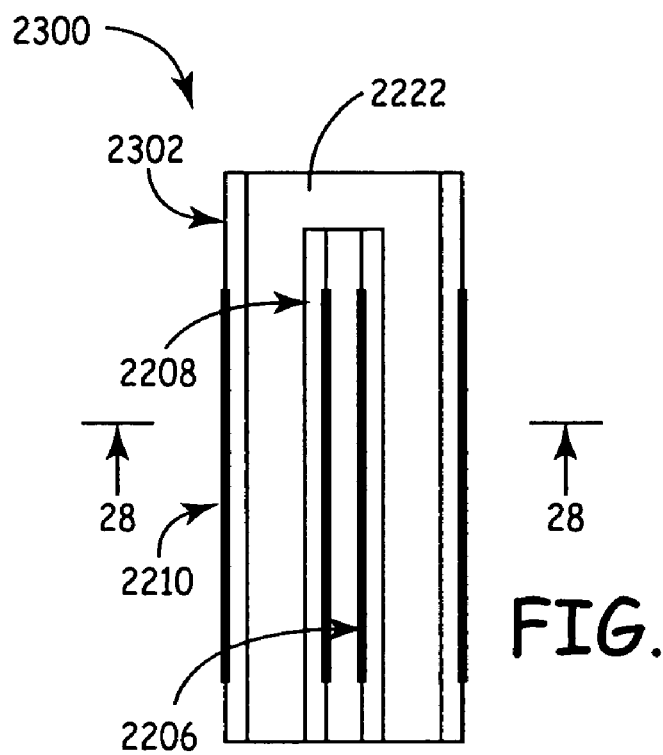
FIG. 27 is a cross-sectional view of a cylindrical NTP cell according to an alternative of the present invention.
Figure 28:
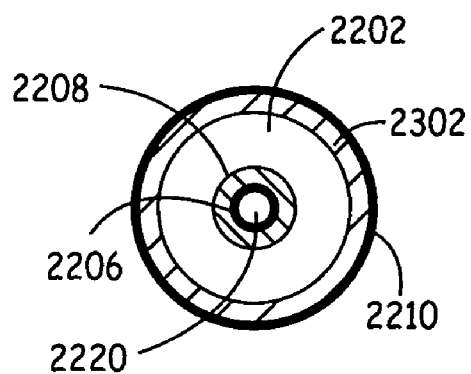
FIG. 28 is a cross-sectional view of the NTP cell taken along lines 28—28 of FIG. 27.

FIG. 27 is a cross-sectional view of a cylindrical NTP cell 2300 according to an alternative of the present invention. FIG. 28 is a cross-sectional view of NTP cell 2300 taken along lines 28—28 of FIG. 27. The same reference numerals are used in FIGS. 27 and 28 as were used in FIG. 26 for the same or similar elements. NTP cell 2300 is similar to NTP cell 2202, but further includes an outer cylindrical dielectric barrier 2302 positioned between reaction volume 2222 and the inner diameter of outer electrode 2210.

Figure 29:
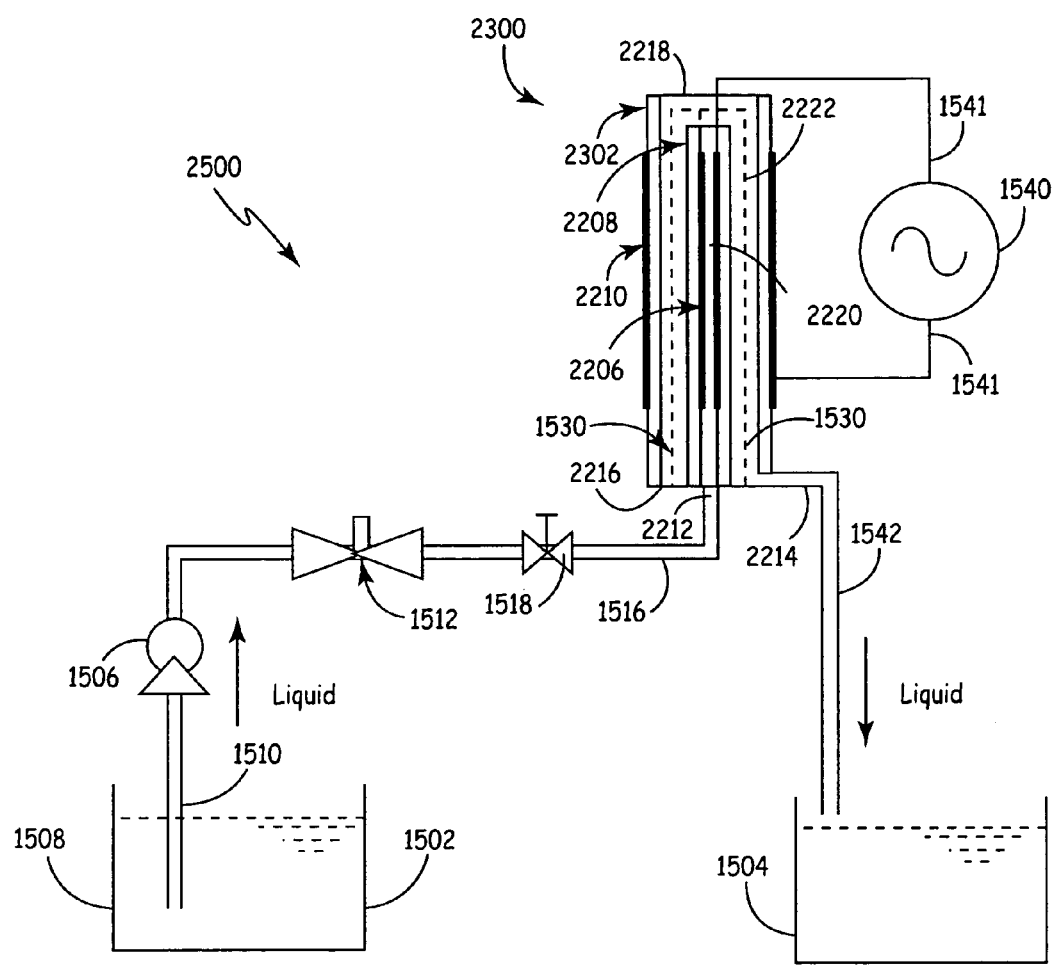
FIG. 29 is a diagram, which schematically illustrates an NTP reactor in which the NTP cell shown in FIGS. 27 and 28 can be used.

FIG. 29 is a diagram, which schematically illustrates an NTP reactor 2500 in which NTP cell 2300 (shown in FIGS. 27 and 28) can be used. Again, the same reference numerals are used in FIG. 29 as were used in FIG. 26 for the same or similar elements.

Figure 30:
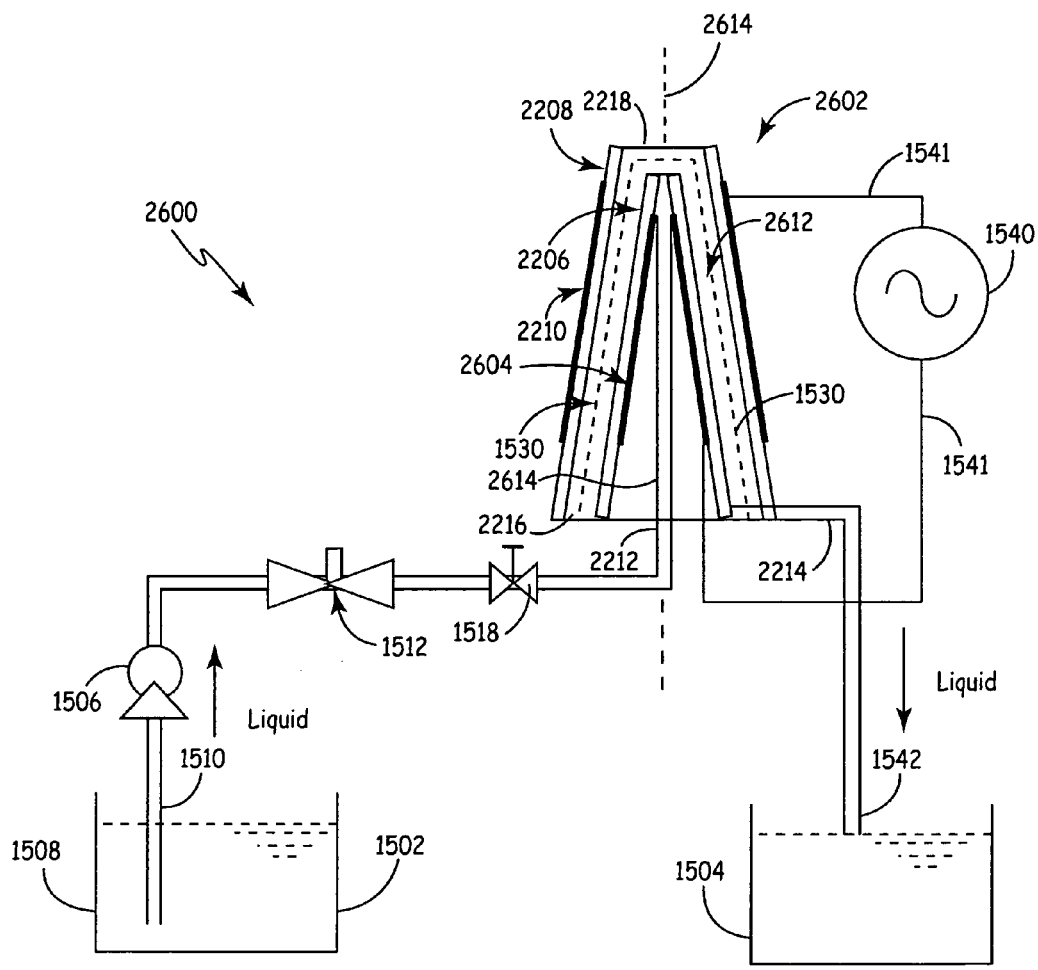
FIG. 30 is a diagram, which illustrates a conical NTP reactor according to another alternative embodiment of the present invention.

FIG. 30 is a diagram, which illustrates a conical NTP reactor 2600 according to another alternative embodiment of the present invention. Reactor 2600 includes a conical NTP cell 2600 having a conical inner electrode 2604, a conical inner dielectric barrier 2606, a conical outer dielectric barrier 2608 and a conical outer electrode 2610. The space between the outer diameter of dielectric barrier 2606 and the inner diameter of dielectric barrier of 2608 defines a reaction volume 2612 through which gas-liquid mixture 1530 passes for treatment. NTP cell 2602 has a central axis 2614, which is aligned vertically similar to the NTP cells shown in FIGS. 26–29. Inlet 2212 is positioned at the base of cell 2602, and includes a passage 2614, which extends through the interior of conical electrode 2604 to the top of reaction volume 2612. In an alternative embodiment, inlet 2212 is positioned at the top of NTP cell 2602. Dielectric barriers 2606 and 2608 isolate electrodes 2604 and 2610 from the gas-liquid mixture 1530 within reaction volume 2612.

In alternative embodiments, the cylindrical or conical NTP cells shown in FIGS. 26–30 can further include one or more dielectric films and discharge initiation regions similar to those shown or described with reference to FIGS. 20 and 21. Also, the cylindrical or conical dielectric barriers can be spaced from their respective electrodes to provide one or more discharge initiation regions between the electrodes and dielectric barriers.

Figure 31:
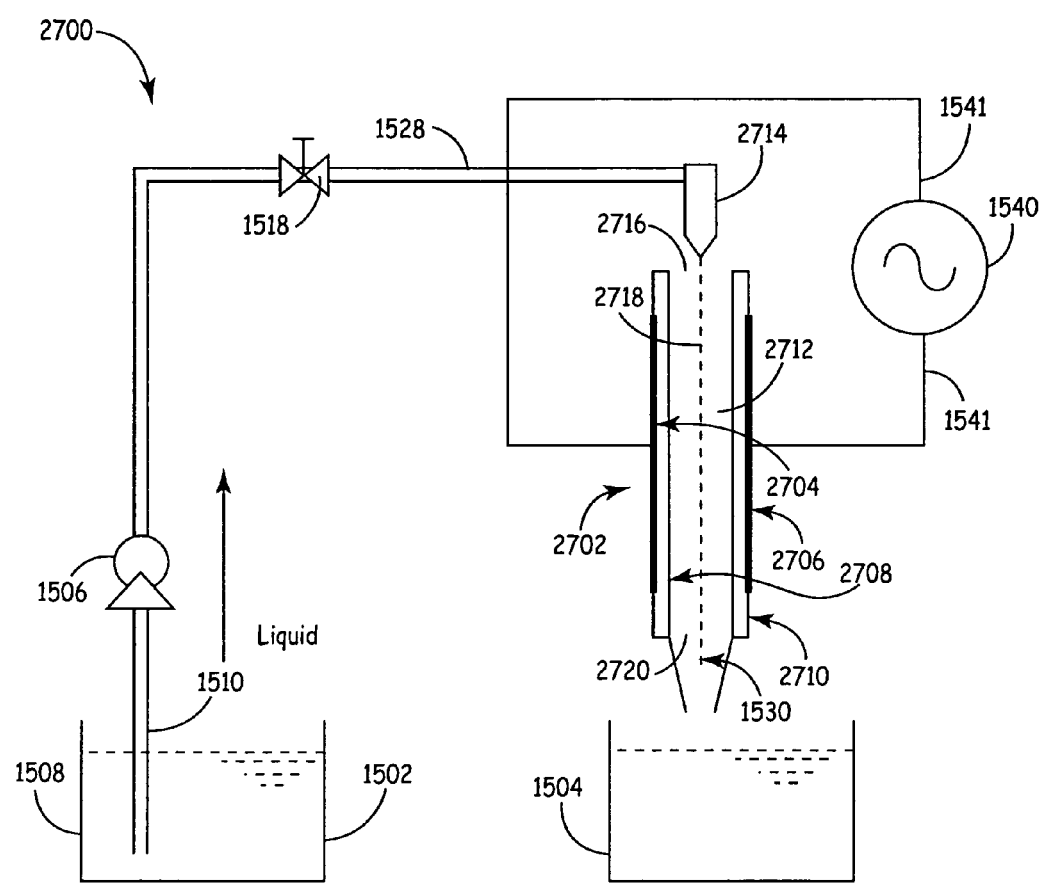
FIG. 31 illustrates a non-thermal plasma reactor in which the liquid is sprayed into the reaction volume, according to another alternative embodiment of the present invention.

FIG. 31 illustrates a non-thermal plasma reactor 2700 in which the liquid is sprayed into the reaction volume, according to another alternative embodiment of the present invention. Reactor 2700 has an NTP cell 2702, which includes vertically aligned electrode plates 2704 and 2706, dielectric barriers 2708 and 2710 and reaction volume 2712. A spraying nozzle 2714 is positioned at a top end 2716 of reaction volume 2712 as is coupled to valve 1518 through tube 1528. Spraying nozzle 2714 sprays the liquid 1508 through reaction volume 2712, between dielectric barriers 2708 and 2710 to form a fine mist 2718 within the reaction volume. Gravity pulls the liquid droplets in mist 2718 downward toward outlet 2720 at which the liquid droplets are returned to tank 1504.

Any of the reactor cell structures discussed in the present application can be used in the NTP reactor 2700 in alternative embodiments of the present invention. NTP cell 2702 can have parallel plate electrodes or concentric cylindrical electrodes, for example, and can have one or more discharge initiator regions as discussed above.

Figure 32:
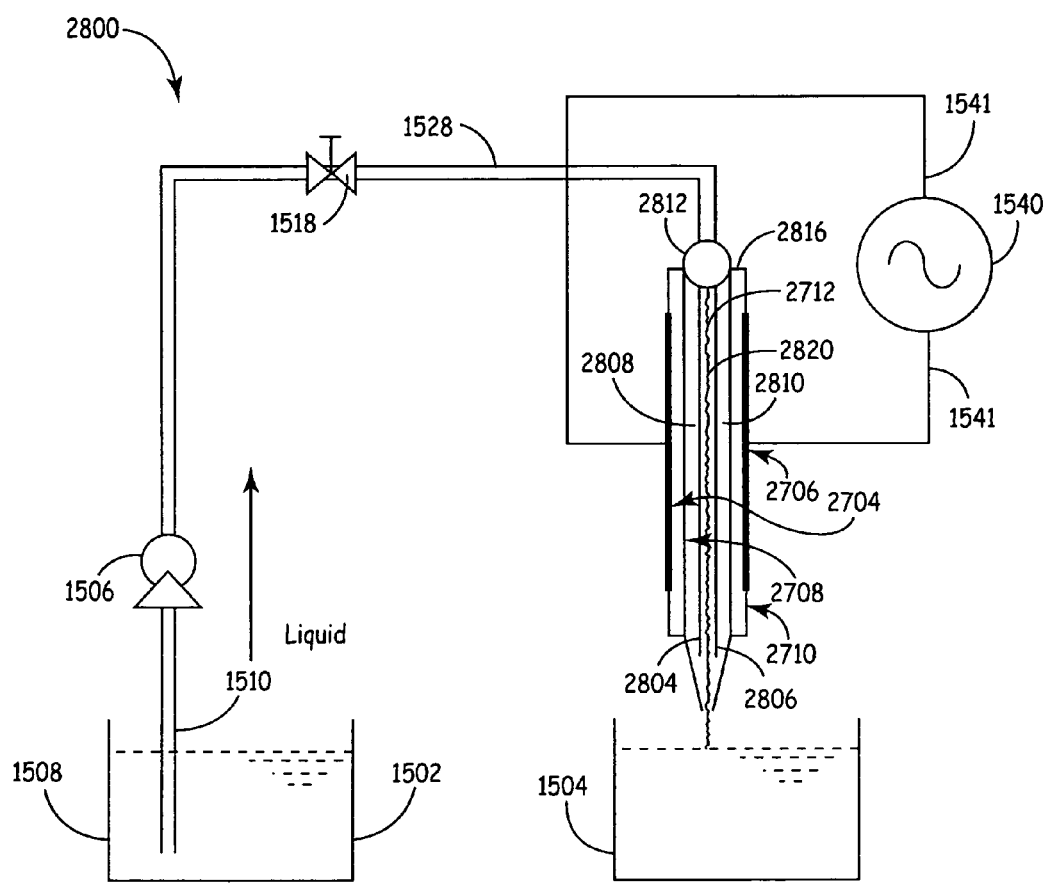
FIG. 32 is a diagram, which illustrates an NTP reactor that forms a liquid curtain according to another alternative embodiment of the present invention.

FIG. 32 is a diagram, which illustrates an NTP reactor 2800 according to another alternative embodiment of the present invention. The same reference numerals are used in FIG. 32 as were used in FIG. 31 for the same or similar elements. Similar to the embodiment shown in FIG. 31, NTP reactor 2800 includes an NTP cell 2802 having vertically aligned electrode plates 2704 and 2706, dielectric barriers 2708 and 2710 and reaction volume 2712. In addition, NTP cell 2802 includes a pair of dielectric films 2804 and 2806, which separate reaction volume 2712 from dielectric barriers 2708 and 2710, respectively. The space between dielectric film 2804 and dielectric barrier 2708 forms a discharge initiation region 2808. Similarly, the space between dielectric film 2806 and dielectric barrier 2710 forms a discharge initiation region 2810.

NTP cell 2802 further includes a thin curtain-forming tube 2812, which is coupled to tube 1528 at the top end 2816 of cell 2802. As tube 1528 delivers liquid 1508 to curtain-forming tube 2812, the liquid falling from tube 2812 forms a "curtain" 2820 of liquid through reaction volume 2712. The curtain of liquid 2820 significantly increases the surface area of the liquid that is exposed to the NTP species and encourages mixing of the liquid with the surrounding gas in reaction volume 2712. The treated liquid returns to tank 1504. Curtain forming tube 2812 can include a horizontal tube with holes in the bottom or with overflow openings along the sides of the tube to form the curtain of liquid. Other structures can also be used to form a continuous or intermittent liquid "curtain".

5. Further Experimental Results

Further experiments were conducted on animal blood samples using a variety of the further reactor embodiments discussed above, and with various operating conditions. For example in one experiment, NTP system 3300 shown in FIG. 33 was used as a test apparatus. System 3300 included a liquid source tank 3302, a pump 3302, NTP reactor 3306 and power supply 3308. Tube 3310 coupled tank 3302 to pump 3304, and tube 3312 coupled pump 3304 with an inlet of reactor 3306. Tube 3314 coupled an outlet of reactor 3306 with tank 3302.

Reactor 3306 had a pair of oppositely polarized electrodes 3320 and 3322, which were separated by a reaction volume 3326. Dielectric barriers 3328 and 3330 electrically and physically isolated electrodes 3320 and 3322 from reaction volume 3326. Electrodes 3320 and 3322 had an area of 920 mm×52 mm, and were separated by a discharge gap of 16 mm. Dielectric barriers 3328 and 3330 had thicknesses of 1.5 mm.

Pump 3304 drew liquid 3336 from tank 3302 through tube 3310 and passed the liquid to reaction volume 3326 through tube 3312. Tube 3314 returned the treated liquid to tank 3302. The upper surface of liquid 3336 in reaction volume 3326 is shown by the dashed line. The volume above the dashed line served as a discharge initiation region. In this experiment, reaction volume 3326 did not include a membrane for separating the discharge initiation region. Also, a gas injector was not used for creating a liquid-gas mixture. However, other experiments were performed with these additional elements, and achieved positive results.

During the experiment, three separate tests were performed. For each test a sample of six hundred milliliters (ml) of fresh cow blood was placed in tank 3302. Each sample included 10 standard units per milliliter (u/ml) of heparin anti-coagulant, and was inoculated with $E.\ coli$ 933 prior to treatment. Each sample had a different total bacteria count. Power supply 3308 energized electrodes 3320 and 3322 with an AC voltage of 16–22 kV at a frequency of 60 Hz. Pump 3304 passed the sample through reactor 3306 at a flow rate of 250 milliliters per minute (ml/min).

The samples were treated for up to three hours, which deviated from the experiments discussed above. In those experiments, a shorter treatment time and a higher electric field were used. It was found that when a high electric field (such as 30 kV) was used, the blood samples coagulated very fast, especially along the surface layer of the sample. In the present experiment, lower energy and longer treatment times were used, which were expected to reduce any adverse impacts on the quality of the treated samples.

Another factor in the present experiment was that the sample was circulated many times through reactor 3306, which inevitably caused recontamination. This, in turn, prolonged the needed treatment time for a given reduction in bacterial count and resulted in unnecessary multiple exposures of the samples to the treatment, which increased potential damage due to the treatment. Although this kind of treatment may not be the most desirable for a practical embodiment, it allowed for a relatively simple and small experimental setup. If re-circulation and recontamination can be avoided, the treatment time would be substantially reduced. For example, the reactor can be made with a longer reaction path for conducting one-pass experiments.

a. Inactivation of $Escherichia\ coli$ ($E.\ coli$)

The following table shows the level of $E.\ coli$ bacterial reduction for the present experiment as a function of treatment time for each sample.

|  | ORIGINAL BACTERIAL COUNT | REDUCTION AFTER 1 HOUR | REDUCTION AFTER 2 HOURS | REDUCTION AFTER 3 HOURS |
| --- | --- | --- | --- | --- |
| SAMPLE 1 | $1.1 \times 10^6$ | 75% | 99% | 99.5% |
| SAMPLE 2 | $1.76 \times 10^6$ | 86% | 98.5% | 99.6% |
| SAMPLE 3 | $6.85 \times 10^5$ | — | — | 99.8% |

Figure 33:
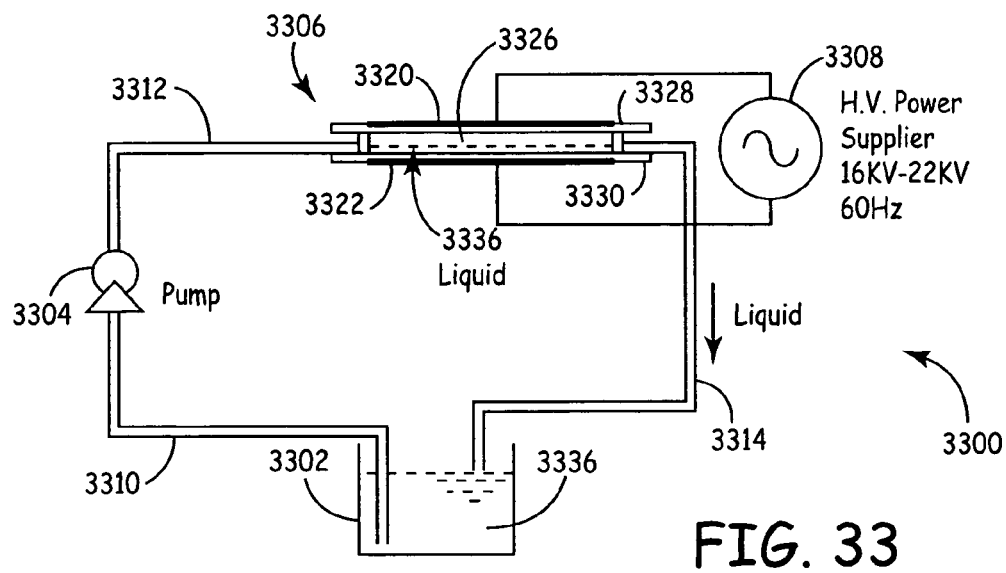
FIG. 33 is a diagram illustrating an experimental test apparatus that was used for testing NTP treatments on fresh cow blood.
Figure 34:
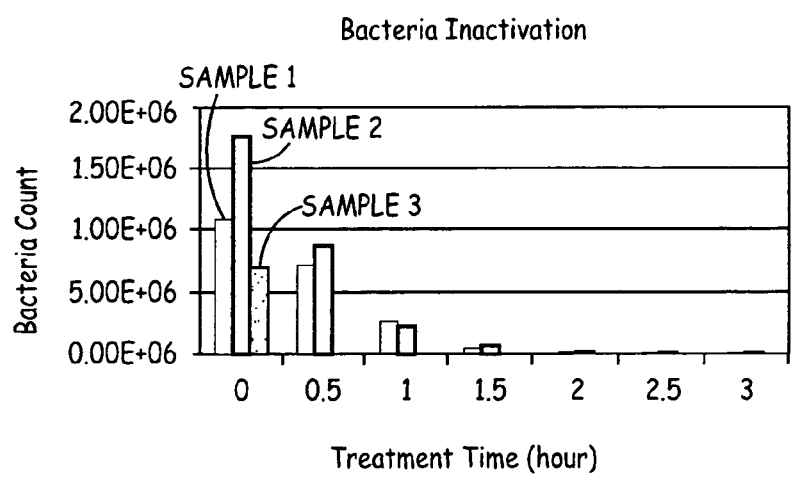
FIG. 34 is a graph illustrating bacterial inactivation for each sample treated in the apparatus shown in FIG. 33 as a function of treatment time.

FIG. 34 is a graph illustrating bacterial inactivation for each sample as a function of treatment time in hours. These results show that a 3-log reduction of $E.\ coli$ bacteria inoculated in cow blood can be achieved using the simple test apparatus shown in FIG. 33.

b. Change in Hematological Properties of Blood Samples

Figure 35:
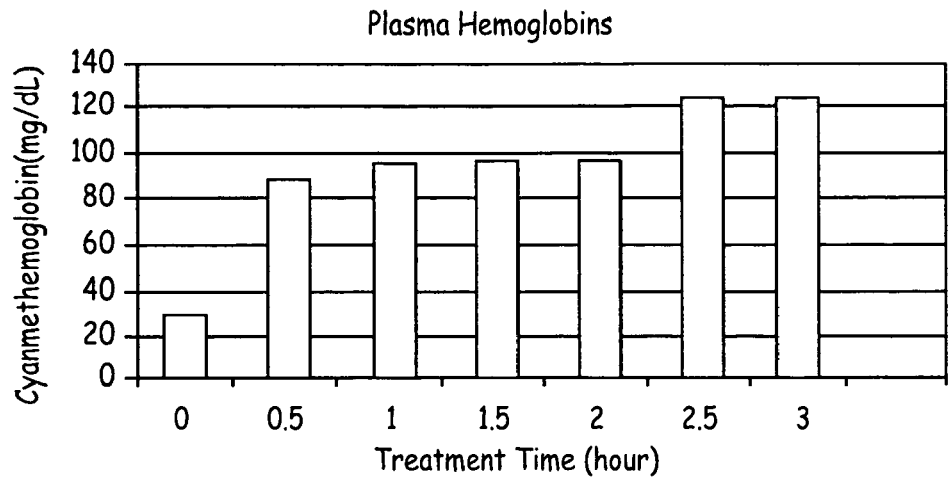
FIG. 35 is a graph illustrating concentration of plasma hemoglobin in the blood samples as a function of treatment time for the apparatus shown in FIG. 33.

FIG. 35 is a graph illustrating concentration of blood plasma hemoglobin in the blood samples as a function of treatment time for the apparatus shown in FIG. 33. The concentration of blood plasma hemoglobins increased with treatment time.

Figure 36:
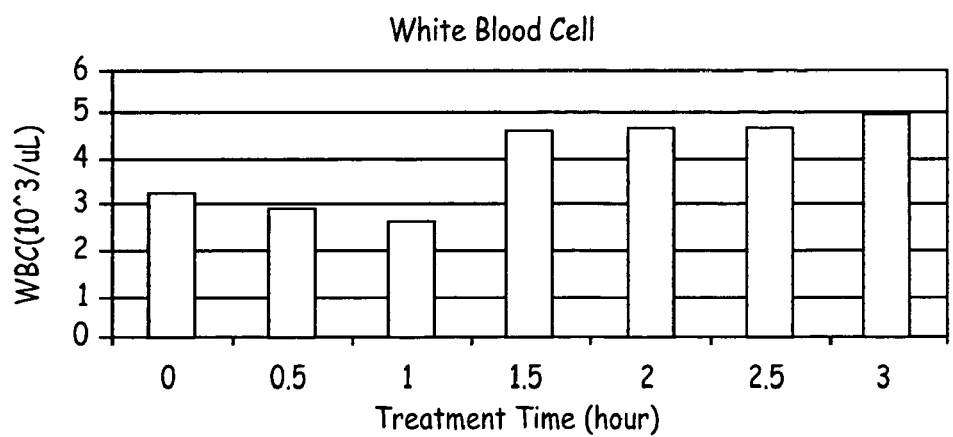
FIG. 36 is a graph illustrating concentration of white blood cells (WBCs) in the blood samples as a function of treatment time.
Figure 37:
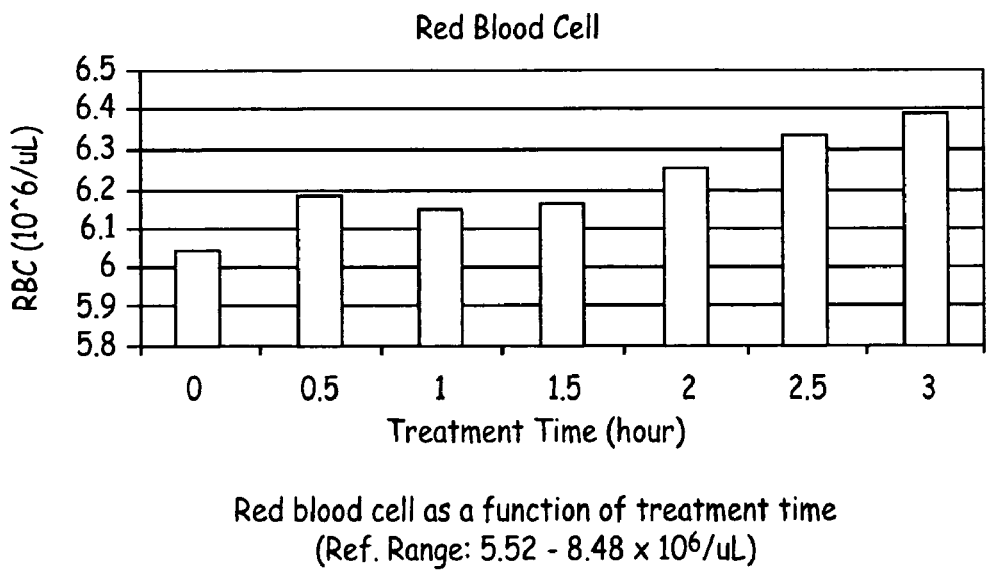
FIG. 37 is a graph illustrating concentration of red blood cells (RBCs) in the blood samples as a function of treatment time.

FIG. 36 is a graph illustrating concentration of white blood cells (WBCs) in the blood samples as a function of treatment time, and FIG. 37 is a graph illustrating concentration of red blood cells (RBCs) in the blood samples as a function of treatment time. The white and red blood cell concentrations remained within the normal reference ranges for these properties following treatment.

Figure 38:
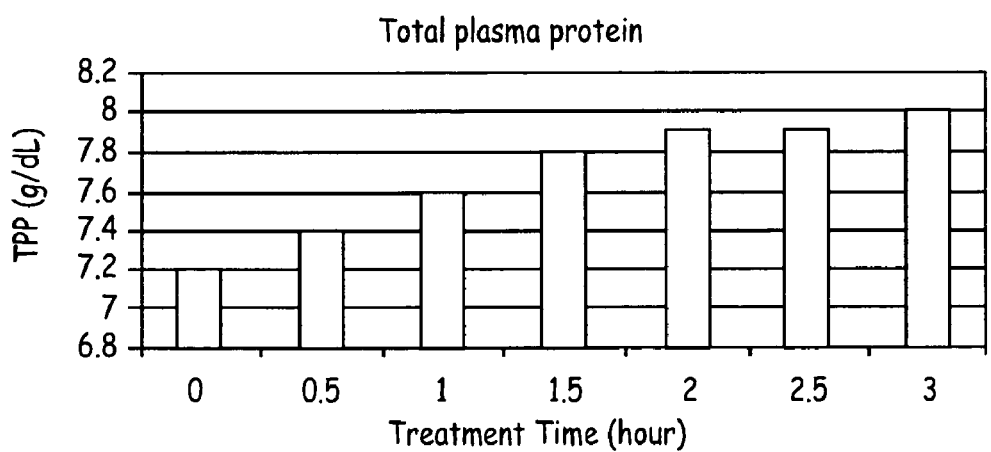
FIG. 38 is a graph illustrating concentration of Total Plasma Protein (TPP) in the blood samples as a function of treatment time.

FIG. 38 is a graph illustrating concentration of Total Plasma Protein (TPP) in the blood samples as a function of treatment time. The Total Plasma Protein concentration changed very little after treatment, and varied only from 7.2 g/dL to 8.0 g/dL, which is within the normal range of 6.8 g/dL to 9.2 g/dL for cow blood.

Figure 39:
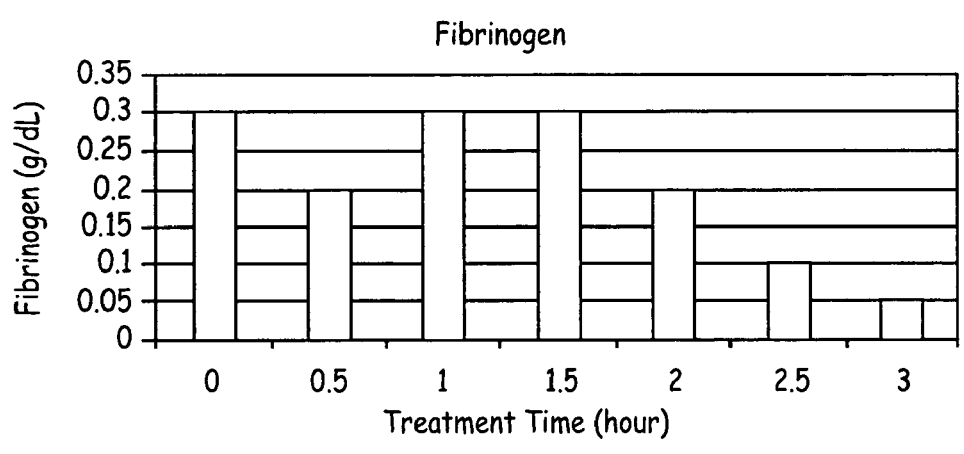
FIG. 39 is a graph illustrating concentration of fibronigen in the blood samples as a function of treatment time.

FIG. 39 is a graph illustrating concentration of fibronigen in the blood samples as a function of treatment time. Again, the fibronigen concentration varied within the allowed range, except after three hours of treatment.

c. Treatment of a Virus

The test apparatus shown in FIG. 33 was also used successfully to treat a virus in water samples. The water samples contained $5.5 \times 10^3$ units per milliliter of Infection Bovine Rhinotracheitis (IBR) virus. A first water sample was passed through NTP reactor 3306 four times, without being re-circulated through a common tank as in FIG. 33. No virus could be detected in the first water sample after the treatment. A second water sample was circulated through the reactor and a common tank 3302 for a period of 40 minutes. Again, no virus could be detected in the second water sample after the treatment. The NTP treatments were therefore effective for killing the IBR virus, even with very brief treatment as in the case of the first water sample.

Non-thermal plasma can therefore be used for at least partially disinfecting biological fluids, such as human and animal blood while leaving most of the hematological properties of the blood within normal ranges following treatment. Any adverse affects on these properties can be reduced by further optimization of the system and its operating parameters.

Since there is substantially no ohmic heating, energy consumption during non-thermal plasma treatment is small, and there is no need to cool the liquid being treated. This allows the system to be easily scaled-up accommodate a very large treatment volume. The desired treatment time can be obtained by passing the liquid through multiple NTP reactors connected together in series with one another, by increasing the reaction volume length, decreasing the flow rate, or by cycling the liquid through the same reactor multiple times. Also, the number of series-connected reaction volumes in the same reactor can be increased or decreased. Because of the non-thermal nature of the system, the system preserves the quality and other heat-sensitive attributes of the liquid. Also, since each electrode is physically and electrically isolated from the liquid being treated, the electrodes do not act as a source of contaminants to the liquids.

In effect, the non-thermal plasma utilizes several different species to inactivate pathogen, including highly reactive species that stabilize immediately upon removing the electric field, some ozone, ultraviolet, photons, and the like. These species do not appear to lead to unsafe excess concentration levels, which would be the case with exclusive exposure to higher levels of any one of these inactivation mechanisms alone. Although ozone is one of the highly reactive species that is generated, the concentration is more limited and the species are very short-lived as compared to more traditional ozonation systems. Lingering ozone may be an advantage for purifying bottled water, but in biological fluids, control of all biochemical process is critical. Non-thermal plasma species virtually all resolve themselves and lose reactivity immediately upon removal of the electric field, making it essentially totally controllable by the treating medical specialist. This allows non-thermal plasma to be used for more time-sensitive treatments of biological fluids where long time periods are not generally available for reducing excess ozone levels in the treated fluid.

Non-thermal plasma can therefore be an effective method of disinfecting biologic fluids using processes that are either replacements for or adjunctive to traditional antibiotic and anti-viral therapies. For example, blood or cerebrospinal fluid can be treated with non-thermal plasma to eliminate bacteria such as *staphylococcus* or viruses without toxicity to the characteristics of the fluids. Another clinical application would be to couple an NTP system in series with a renal dialyzer. Non-thermal plasma can be used to treat severe blood-borne infections when drugs are not indicated, or to disinfect donated blood in blood bank storage, increasing the usable supplies. Treatment can be performed as the blood is drawn from the donor, at the blood bank, or as the blood is transfused into the receiving patient. It is also possible that non-thermal plasma can potentially be used as an adjunctive (supporting) therapy to assist with the treatment of bacterial meningitis, where there is a need to stay ahead of the rapid bacterial reproduction and spread without poisoning the patient with the bacterial toxins.

Further examples of possible non-thermal plasma treatments include: 1) treatment of peritonitis (quasi-dialyzing by injecting sterile water or other dialysate compositions into the peritoneal cavity and cycling the water through an endoscope or catheter having an associated internal or external NTP reactor); 2) treatment of Septicemia (e.g., by coupling an NTP reactor in series with a hemodialysis apparatus); 3) treatment of a liver or gall bladder abcess endoscopically, such as by cycling bile, etc. through a lumen in the endoscope and treating the bile with non-thermal plasma; 4) treating hepatitis by injecting sterile saline or other fluidic agents into the liver and processing liver fluids in vivo with non-thermal plasma; 5) treating viral or bacterial meningitis; and 6) treating lymph by processing the lymph with non-thermal plasma and feeding it back into the bloodstream through the thoracic duct, for example. Numerous other applications exist.

Figure 42:
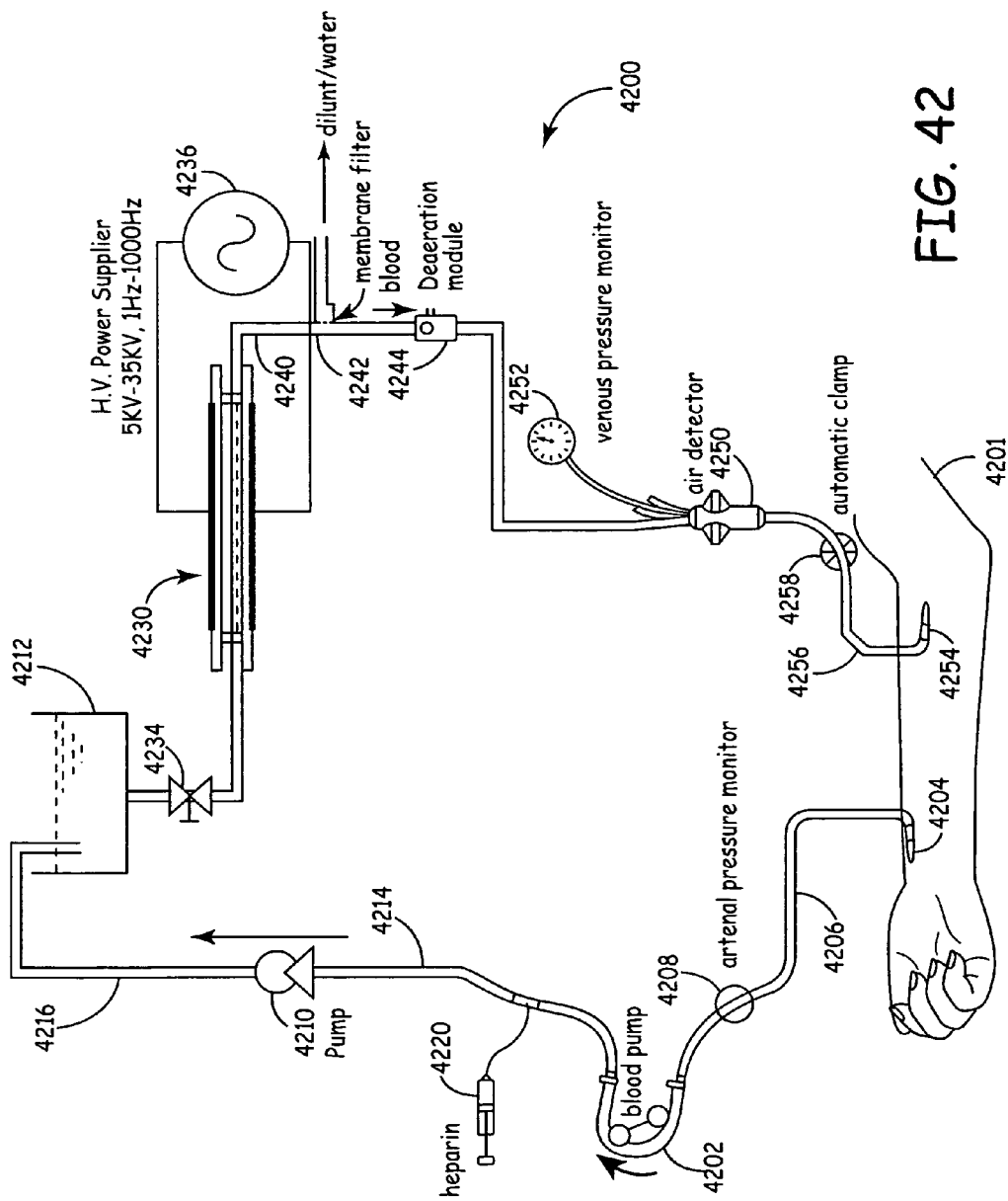
FIG. 42 is a diagram illustrating an ex-vivo circulatory system and method for disinfecting the blood of a live mammal patient using non-thermal plasma according to another embodiment of the present invention.

For example, when blood is treated using the hemodialysis-type blood pasteurization system described by FIGS. 2, 18 and 42, for example, which could utilize any of the different described NTP reactor chambers, in conjunction with the other circulating and filtering mechanisms shown, the blood is diluted for improved flow and clotting resistance. After treatment, the diluted blood is applied to a semi-permeable membrane having openings for filtering-out the diluent, common blood-born bacteria and/or other toxins in the blood, as described in more detail with respect to FIGS. 18 and 42.

Non-thermal plasma can also be used in conjunction with a single, double or triple lumen probe or catheter, for example, with non-thermal plasma electrodes on the distal end or positioned along one or more of the lumens. These probes can be inserted endoscopically into a diseased organ, an artery or vessel, for example, and local fluids can be treated with non-thermal plasma by positioning the electrode adjacent the area in the body to be treated or by pumping bodily fluids through reaction volume within a lumen to destroy undesirable elements, in place of open surgery. The electrodes can be placed directly on inflamed tissue to shower the tissue with reactive species (e.g., oxygenated radicals, etc.) while they are still reactive. For example, a surface non-thermal plasma electrode (with alternating-polarity conductors along its surface) can be used to generate a surface non-thermal plasma that can be used to treat the tissue. This surface non-thermal plasma electrode can be positioned on the distal end of an instrument, for example, which is inserted into the body. Other structures and treatment methods can also be used.

Figure 40:
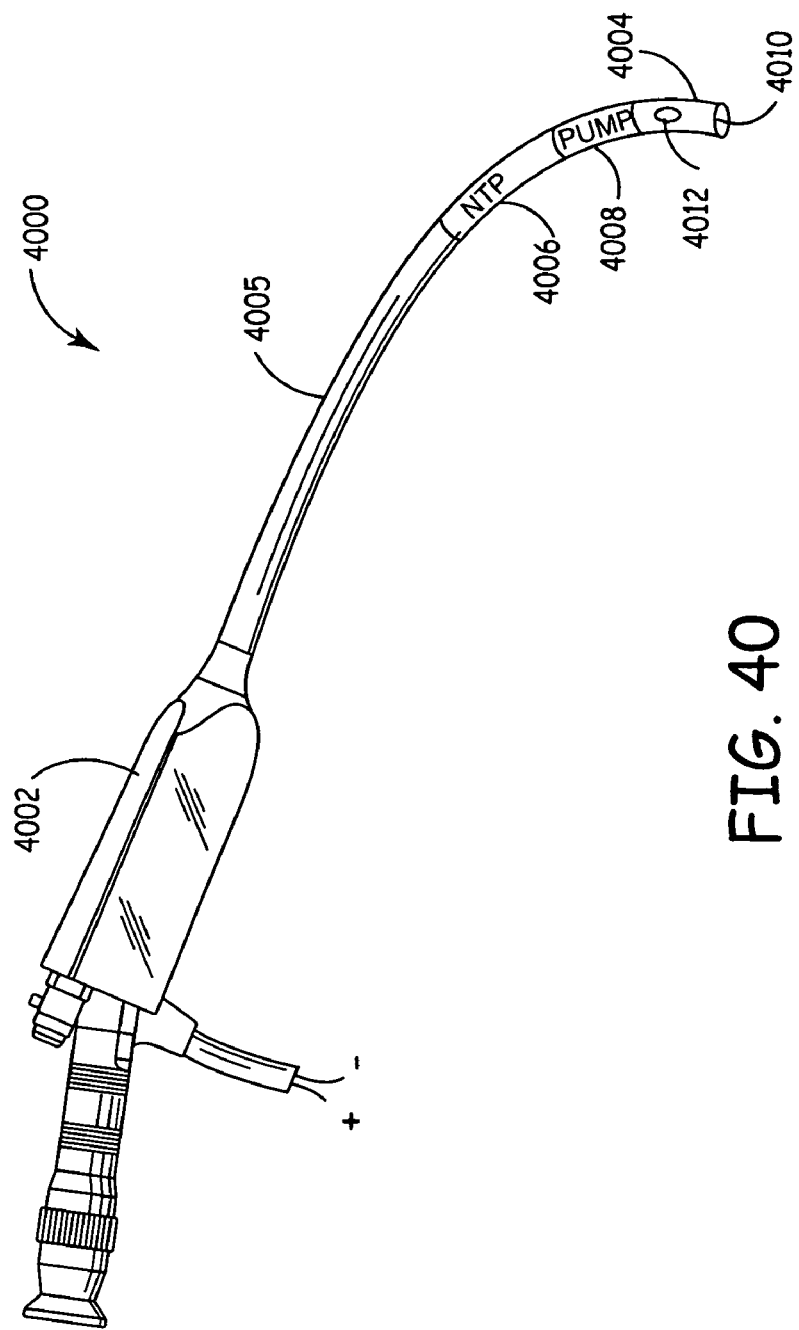
FIG. 40 is a diagram, which schematically illustrates a catheter that can be used for in-vivo NTP treatment according to one embodiment of the present invention.

FIG. 40 is a diagram, which schematically illustrates an elongated probe 4000 that can be used for in-vivo NTP treatment according to one embodiment of the present invention. The shaft can include any medical instrument, catheter or endoscope-type device, with or without an internal lumen, which can be used to access an internal cavity, such as the interior of a hollow organ or lumen, of a mammal. In this example, probe 4000 includes a proximal end 4002, a distal end 4004, an NTP reactor 4006 carried along the shaft, and a pump 4008. When the shaft of probe 4000 is inserted into an organ, artery or other region of a patient, pump 4008 draws fluid from inlet 4010 and passes the fluid through NTP reactor 4006 to outlet 4012. The treated fluid is then returned to the patient from outlet 4012. Inlet 4010 and outlet 4012 can be positioned anywhere along probe 4000, and the particular arrangement would depend on the procedure being performed and the desired flow pattern into and out of the shaft. Similarly, NTP reactor 4006 and pump 4008 can be positioned anywhere on or in probe 4000 or external to shaft 4000. Also, pump 4008 can be positioned anywhere along the fluid travel path between inlet 4010 and outlet 4012. Probe 4000 can be a stand-alone device for NTP treatment or can be combined with the function of another medical instrument. Probe 4000 can have one or more lumens for passing the fluid to be treated and can have additional lumens or elements as desired.

Figure 41:
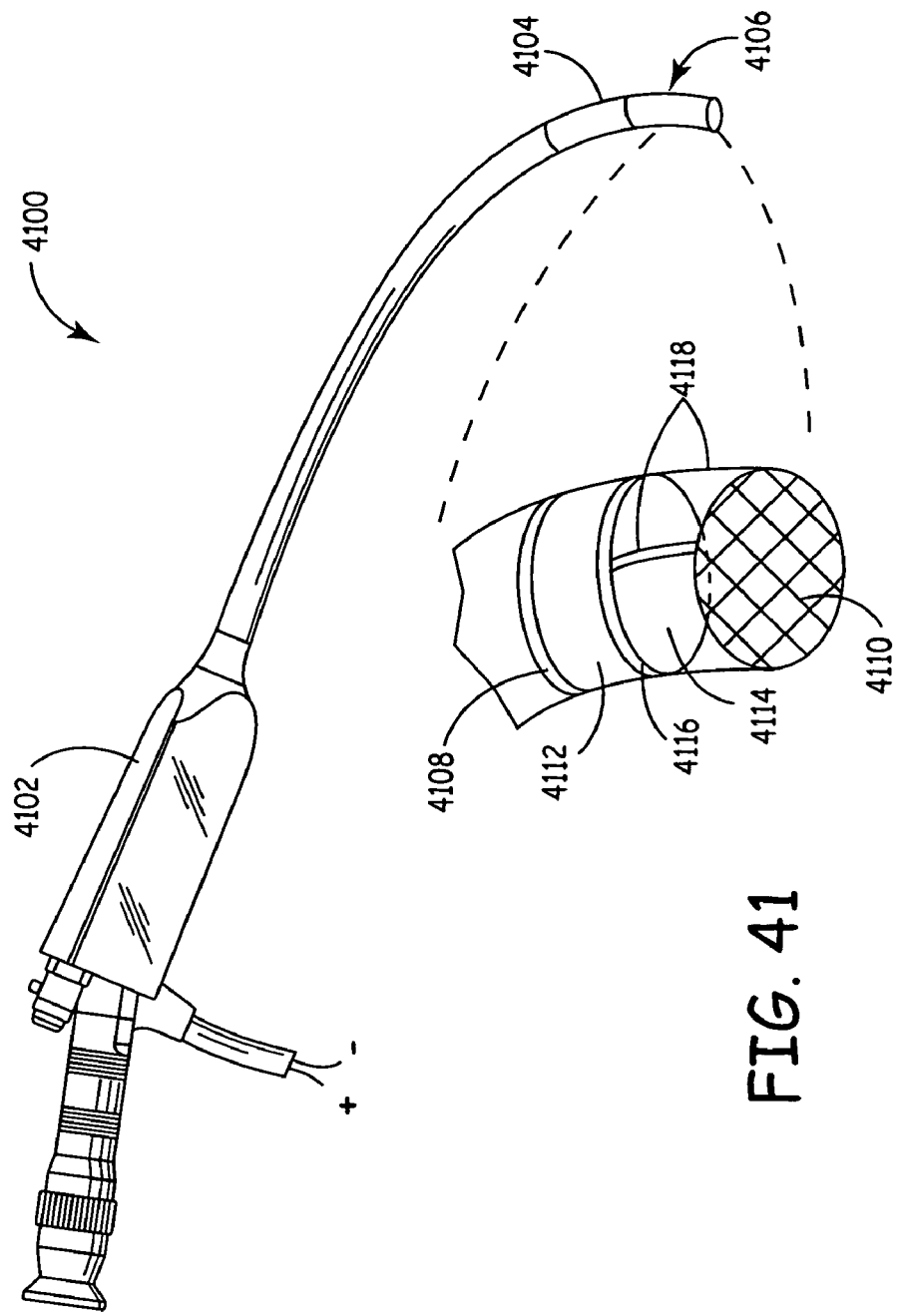
FIG. 41 is a diagram, which schematically illustrates a further catheter that can be used for in-vivo NTP treatment according to an alternative embodiment of the present invention.

FIG. 41 is a diagram, which schematically illustrates a probe 4100 that can be used for in-vivo NTP treatment according to another embodiment of the present invention in which no pump is needed. Probe 4100 includes a shaft with a proximal end 4102, a distal end 4104 and an NTP reactor 4106. Similar to the embodiment shown in FIG. 16, for example, reactor 4106 includes oppositely polarized electrodes 4108 and 4110, a discharge initiation region 4112, a treatment region 4114 and a separating film 4116. However, electrode 4110 is formed of a wire mesh, which is supported on the distal end of the shaft by one or more support beams 4118, for example, to promote the flow of fluid into and out of treatment region 4114. With this structure, the perimeter of treatment region 4114 is open to an exterior of probe 4100. Electrode 4110 can be bare conductive material or coated with a dielectric material, for example. Film 4116 isolates discharge initiation region 4112 from treatment region 4114. In one embodiment, discharge initiation region 4112 is bounded by electrode 4108, film 4116 and the sidewall of probe 4100. Fluid entering treatment region 4114 is exposed to the NTP species generated across treatment region 4114 and those species that are generated in initiation region 4112 and pass through film 4116. During treatment, the distal end 4104 of probe 4100 can be moved in and around the area of the body to be treated. For example, the distal tip can be swept through a locally infected area such as a liver, lung, or abdomen for killing sufficient concentrated pathogens to reduce the viral load to a level that is within the body's immune system capacity. Such an instrument could also process blood flowing into the vena cava from the lymph system.

Numerous other instrument structures can be used for facilitating in-vivo NTP treatment in further alternative embodiments of the present invention. The fact that the NTP species only remain active during roughly the time when the electrical field is powered can help to limit adverse effects of the treatment.

FIG. 42 is a diagram illustrating one system and method 4200 for ex-vivo disinfecting blood of a live human or animal patient using non-thermal plasma according to another embodiment of the present invention. System 4200 is a circulating ex-vivo hemodialysis-type of apparatus, which draws blood from the circulatory system of a live patent 4201 through one or more arteries, for example, treats the blood with non-thermal plasma and returns the disinfected blood to the patient. The NTP system can achieve substantial reduction in bacterial or viral loads with fewer attendant complications, such as clotting, excess destruction of desired blood fractions, antibiotic resistance, etc. This ex vivo blood treatment could filter out bacterial toxins released before returning the blood to the body because of the disparity in size between bacteria and its products, and the essential solid blood fractions. After treatment, any additional required fluids and lipids can be provided via intravenous (I.V.) application.

NTP system 4200 includes a blood pump 4202 for drawing blood from patient 4201 through a shunt 4204 and a tube 4206. An arterial pressure monitor 4208 can be coupled to tube 5206 for monitoring pressure within the patient's circulatory system during the procedure. A further pump 4210 pumps the blood drawn from patient 4201 by blood pump 4202 to a reservoir tank 4212 through tubes 4214 and 4216. In one embodiment, a temperature-conditioned diluent 4220 is added to the blood along tube 4214 until the blood is translucent, for example. Diluent 4220 can include sterile water, an anti-coagulant (such as heparin) and other elements as needed. Reservoir tank 4212 stores the diluted blood for treatment. The diluent makes the fluid less opaque so that photons generated in reactor 4230 can have better effect, and also improves the flow characteristics and reduces potential clotting levels within the apparatus.

The diluted blood passes from tank 4212 to NTP reactor 4230 through tube 4232 and gas injector 4234. Gas injector 4234 injects a gas into the diluted blood as described above with respect to FIGS. 2 and 3, for example. NTP reactor 4230 can have any suitable structure. In one embodiment, NTP reactor 4230 is similar to reactor 1600 shown in FIG. 22, which has separate treatment and discharge initiation regions. The treatment region of NTP reactor 4230 can have multiple parallel paths for the diluted gas-blood mixture to optimize throughput and can have consecutive chambers to increase disinfection in each cycle. As many consecutive chambers can be used as are safe and efficacious. NTP reactor 4230 is driven by a continuous A.C. power supply 4236 having an output voltage of 5 kV to 35 kV and a frequency of 1 Hz to 1000 Hz, for example, to generate cool non-thermal plasma as the diluted gas-blood mixture passes through the reactor.

After NTP treatment application by reactor 4230, the diluted gas-blood mixture is filtered to remove the diluent and the physically small toxin molecules while preserving the red and white blood cells and other benefitial blood components. For example, the diluted gas-blood mixture can be pumped under pressure through tube 4240 and past a semi-permeable membrane within filter 4242. The membrane passes some of the diluent, which carries with it small particles such as bacteria and toxic protein molecules but not all blood plasma and not the larger molecules such as erythrocytes, leukocytes, platelets, etc. The pore size and other characteristics of the membrane can be selected as desired for the particular procedure being performed. In one embodiment, the pores range in size from 0.1 to 2 micrometers, for example, which are capable of passing the most common blood-borne bacteria. *Staphylococcus* molecules are spherically-shaped, and about 0.75 micrometers in size, while *E-coli* are elongated "rounded cylinders" about 0.5 micrometers in diameter by 2 micrometers in length. The toxin proteins and other molecules they release upon cell lysis are much smaller, allowing passage through the filter spaces in the membrane. Solid blood fractions, on the other hand, are much larger than bacteria or proteins: RBCs (erythrocytes) are 6–8 microns in diameter, and WBCs range in size from 6 to 16 microns, preventing them from passing through with the waste and excess water. Some platelets, sized between 1 and 4 microns, may be lost with the excess water and toxic waste, but most will be retained. The optimal opening size can be determined based on desired final treated blood composition.

After filtering, the blood can then be tested for pathogen concentration and either membrane-filtered again or passed to de-aeration module 4244 for removing the gas from the gas-blood mixture.

The de-gassed, re-concentrated blood can then be returned to the patient's body. In one embodiment, the de-gassed, re-concentrated blood first passes through a gas detector 4250 and venous pressure monitor 4252 before being returned to a vein of patient 4201 through a shunt 5254 and a tube 4256. If any gas remains in the blood, clamp 5258 can be closed automatically to prevent the gas from being delivered to the patient. Also, clamp 4258 can be used to maintain a desired venous pressure within patient 4201 as measured by monitor 5252. As the blood is returned to the body, it can also be tested for electrolyte and lipid levels and those levels enhanced as needed.

The process shown in FIG. 42 can involve multiple chambers in reactor 4230 or multiple passes through the body and back through system 4200 as to best cleanse the blood. System 4200 can have various arrangements and elements in alternative embodiments of the present invention. The gas composition, level of dilution, and flow rates can be traded off with electric field strength to optimize the system performance with regard to time, pathogen kill-rate, and patient tolerance of the process.

A variety of diseases or pathogens could be treated with NTP using an apparatus similar to those discussed herein or modified to suit the particular treatment. These diseases include any fluid-borne pathogen that can be destroyed with non-thermal plasma generated by one or more electrodes that are electrically isolated from the treated liquid by a dielectric. Different types of gasses can be introduced to the liquid being treated through the gas source (e.g., bubbler or gas injector), depending on desired inactivation effect (target pathogen). In some embodiments, the liquid being treated is not mixed with a gas. Also, certain selected human or other animal blood characteristics can be modified as desired through the use of NTP, such as the variance of white blood cell count.

In addition, embodiments of the present invention provide a pasteurization process that is able to cycle fluids such as blood through an apparatus outside the body to destroy bacterial infection, filter out the toxins released in the process, and then return the cleansed biologic fluid back to the patient in a process that is reasonably compatible with circulatory system time cycles. This process has the potential to provide significant anti-infective benefit, whether as a primary therapy or as an adjuvant supporting treatment used in conjunction with modified dosages of drugs or in cases where the patient's immune system cannot tolerate the bacterial toxin releases that accompany drug therapy.

Although the present invention has been described with reference to preferred embodiments, workers skilled in the art will recognize that changes may be made in form and detail without departing from the spirit and scope of the invention.

What is claimed is:

1. A method of at least partially disinfecting biological fluid of a mammal, which comprises pathogens, the method comprising:
   (a) dispersing the biological fluid in a gas or dispersing the gas in the biological fluid to form a liguid-gas mixture; and
   (b) contacting a non-thermal plasma with the liquid-gas mixture within a reaction volume to kill at least a portion of the pathogens within the biological fluid.

2. The method of claim 1 wherein the biological fluid comprises a blood component.

3. The method of claim 1 and further comprising:
   (c) drawing the biological fluid from the mammal prior to placing the biological fluid in the reaction volume; and
   (d) returning the biological fluid to the mammal after treating the biological fluid in step (b).

4. The method of claim 3 wherein:
   step (c) comprises drawing the biological fluid from a blood circulatory system of the mammal; and
   step (d) comprises returning the biological fluid to the blood circulatory system.

5. The method of claim 3 wherein:
   step (c) comprises drawing the biological fluid from an organ of the mammal; and
   step (d) comprises returning the biological fluid to the organ.

6. The method of claim 1 wherein steps (a) and (b) are performed internal to the mammal.

7. The method of claim 1 wherein the reaction volume is defined in a non-thermal plasma reactor and wherein the method further comprises:
   (c) carrying the non-thermal plasma reactor along an elongated shaft;
   (d) inserting a portion of the shaft into the mammal in which the biological fluid is located; and
   (e) performing steps (a) and (b) while the portion of the shaft is inserted into the mammal.

8. The method of claim 7 wherein step (e) comprises drawing the biological fluid into the shaft, passing the biological fluid through the reaction volume and then removing the biological fluid from the shaft after treatment in step (b).

9. The method of claim 1
   (c) wherein step (a) comprises introducing gas bubbles into the biological fluid to generate the liquid-gas mixture.

10. The method of claim 9 and further comprising:
    (e) removing the gas bubbles from the fluid-gas mixture after treating during step (d).

11. The method of claim 1 and further comprising:
    (c) introducing a diluent into the biological fluid to generate a diluted biological fluid;
    (d) treating the diluted biological fluid with the non-thermal plasma during step (b); and
    (e) removing the diluent from the diluted biological fluid after treating during step (d).

12. The method of claim 11 wherein step (e) comprises passing the diluted biological fluid along a semi-permeable membrane having pore sizes that filter the diluent and pathogens having selected sizes from larger components of the biological fluid.

13. The method of claim 1 wherein:
    step (b) comprises passing the biological fluid through the reaction volume between first and second electrodes while maintaining a gap in the reaction volume between the biological fluid and at least one of the first and second electrodes; and
    step (b) comprises electrically exciting the first and second electrodes to generate the non-thermal plasma within the reaction volume.

14. The method of claim 13 and further comprising:
    (c) providing a barrier in the reaction volume, which separates the reaction volume into a discharge initiation region and a treatment region, wherein the discharge initiation region defines the gap and is positioned between the first electrode and the treatment region, and the treatment region is positioned between the discharge initiation region and the second electrode; and wherein step (b) comprises passing the biological fluid through the treatment region.

15. The method of claim 14 wherein the barrier comprises a dielectric material.

16. The method of claim 13 wherein step (b) comprises applying a substantially constant AC or DC voltage to the first and second electrodes.

17. The method of claim 1 wherein step (b) comprises reducing a number of the pathogens in the biological fluid by at least one log.

18. A circulating blood disinfection apparatus for at least partially disinfecting blood of a mammal, the apparatus comprising:

a first shunt for coupling to a circulatory system of the mammal and having a blood outlet;

a second shunt for coupling to the circulatory system of the mammal and having a blood inlet;

an inlet path coupled to the blood outlet of the first shunt for carrying the blood to be disinfected;

an outlet path coupled to the blood inlet of the second shunt for returning the blood to the mammal;

a non-thermal plasma reactor comprising an inlet coupled to the inlet path, an outlet coupled to the outlet path, first and second electrodes, at least one dielectric barrier between the first and second electrodes, and a reaction volume between the first and second electrodes, wherein the reaction volume is coupled to the inlet and the outlet; and a filter in the outlet path, which filters toxins having selected sizes from larger components of the blood.

19. The apparatus of claim 18 wherein the non-thermal plasma reactor further comprises a discharge initiation region and a treatment region, wherein the discharge initiation region is positioned between the first electrode and the treatment region, and the treatment region is positioned between the discharge initiation region and the second electrode, and wherein the treatment region is coupled to the inlet and the outlet.

20. The apparatus of claim 19 wherein the non-thermal plasma reactor further comprises a barrier separating the discharge initiation region from the treatment region.

21. The apparatus of claim 18 and further comprising:

a gas injector coupled in the inlet path and having a gas inlet for receiving a gas to be injected into the blood being passed along the inlet path; and a gas-liquid separator coupled along the outlet path.

22. The apparatus of claim 18 and further comprising:

a diluent inlet along the inlet path for receiving a diluent to be mixed with the blood; and wherein the filter comprises a membrane filter coupled along the outlet path and adapted to filter at least a portion of the diluent from the blood along the outlet path.

23. The apparatus of claim 22 wherein the membrane filter comprises a semi-permeable membrane having pore sizes that are smaller than the sizes of red and white blood cells.

24. A probe for insertion into a mammal, the probe comprising:

a shaft with a proximal end and a distal end;

an inlet and an outlet positioned along the shaft; and a non-thermal plasma reactor carried along the shaft and comprising first and second electrodes, at least one dielectric barrier between the first and second electrodes, and a reaction volume between the first and second electrodes, wherein the reaction volume is coupled to the inlet and the outlet.

25. The probe of claim 24 and further comprising a pump located along a fluid travel path extending between the inlet and the outlet.

26. The probe of claim 24 wherein the non-thermal plasma reactor further comprises a discharge initiation region and a treatment region, wherein the discharge initiation region is positioned between the first electrode and the treatment region, and the treatment region is positioned between the discharge initiation region and the second electrode, and wherein the treatment region is coupled to the inlet and the outlet.

27. The probe of claim 26 wherein the non-thermal plasma reactor further comprises a barrier separating the discharge initiation region from the treatment region.

28. The probe of claim 27 wherein the treatment region is located at the distal end of the shaft and has a perimeter that is open to an exterior of the probe and defines the inlet and the outlet.

29. A biological fluid treatment apparatus comprising:

a biological fluid input for receiving biological fluid of a mammal, which comprises pathogens in the biological fluid;

means for introducing gas bubbles into the biological fluid received from the biological fluid input to produce a mixture of the biological fluid and the gas bubbles;

non-thermal plasma reactor means for receiving the mixture of the biological fluid and the gas bubbles within a reaction volume and for generating a non-thermal plasma within the reaction volume to thereby kill at least a portion of the pathogens within the biological fluid; and a gas-liquid separator coupled to an output of the reactor means for separating the gas bubbles from the biological fluid.

* * * * *